US007790399B2

(12) United States Patent
Bourel et al.

(10) Patent No.: US 7,790,399 B2
(45) Date of Patent: Sep. 7, 2010

(54) PREPARATION OF HUMAN, HUMANIZED OR CHIMAERIC ANTIBODIES OR POLYPEPTIDES HAVING DIFFERENT BINDING PROFILES TO FCGAMMA RECEPTORS

(75) Inventors: Dominique Bourel, La Madeleine (FR); Christophe De Romeuf, Lille (FR); Sophie Siberil, Paris (FR); Wolf Herman Fridman, Paris (FR); Jean-Luc Teillaud, Paris (FR); Nicolas Bihoreau, Orsay (FR); Emmanuel Nony, Antony (FR)

(73) Assignees: Laboratoire Francais du Fractionnement et des Biotechnolgies (LFB), Les Ulis (FR); Institut National de la Sante et de la Recherche Medicale (INSERM), Paris (FR)

( * ) Notice: Subject to any disclaimer, the term of this patent is extended or adjusted under 35 U.S.C. 154(b) by 621 days.

(21) Appl. No.: 10/551,819

(22) PCT Filed: Apr. 5, 2004

(86) PCT No.: PCT/IB2004/001390

§ 371 (c)(1),
(2), (4) Date: Jun. 12, 2006

(87) PCT Pub. No.: WO2004/087757

PCT Pub. Date: Oct. 14, 2004

(65) Prior Publication Data

US 2007/0135621 A1    Jun. 14, 2007

(30) Foreign Application Priority Data

Apr. 3, 2003    (EP) .................................. 03290834

(51) Int. Cl.
*G01N 33/53* (2006.01)
(52) U.S. Cl. .................................................... 435/7.1
(58) Field of Classification Search ........................ None
See application file for complete search history.

(56) References Cited

U.S. PATENT DOCUMENTS

| 7,541,029 | B2 * | 6/2009 | Beliard et al. ............. 424/130.1 |
| 7,579,170 | B2 * | 8/2009 | Beliard et al. ............. 435/70.21 |
| 2003/0175969 | A1 * | 9/2003 | Beliard et al. ................. 435/455 |
| 2006/0127392 | A1 * | 6/2006 | de Romeuf et al. ....... 424/133.1 |
| 2007/0009522 | A1 * | 1/2007 | Beliard et al. ............. 424/144.1 |

FOREIGN PATENT DOCUMENTS

| EP | 0 481 790 A | 4/1992 |
| WO | WO 97/28267 A | 8/1997 |
| WO | WO 99/58572 A | 11/1999 |
| WO | WO 01/77181 A | 10/2001 |

OTHER PUBLICATIONS

Shinkawa et al. JBC Jan. 31, 2003;278(5):3466-73. Epub Nov. 8, 2002.*
Shinkawa et al., J. Biol. Chem., 2003, 278: 3466-3473.*
Davies et al., "Expression of GnTIII in A Recombinant Anti-CD20 CHO Production Cell Line: Expression of Antibodies with altered Gycoforms Leads To An Increase in ADCC Through Higher Affinity of FcgammaRIII," Biotechnology and Bioengineering Combinatoial Chemistry, vol. 74, No. 4, Aug. 2001, pp. 288-294.
Shields et al., "Lack of Fucose on Human IgG1 N-Linked Oligosaccharide Improves Binding to Human FcgammaRIII and Antibody-Dependent Cellular Toxicity," Journal of Biological Chemistry, American Society of biological Chemists, vol. 277, No. 30, Jul. 26, 2002, pp. 26733-26740.
Wright et al., "Effect of Glycosylation on Antibody Function: Implications for Genetic Engineering," Trends in Biotechnology, Elsevier Publications, vol. 15, No. 1, 1997, pp. 26-32.
Shields et al., "High Resolution Mapping of the Binding Site on Human IgG1 for FcyRI, FcyRII, FcyRIII, and FcRn and Design of IgG1 Variants with Improved Binding to the FcyR," *Journal of Biological Chemistry*, vol. 276, No. 9, pp. 6591-6604 (Mar. 2, 2001).
Randaev et al., "The Structure of a Human Type III Fcy Receptor in Complex with Fc," *Journal of Biological Chemistry*, vol. 276, No. 19, pp. 16469-16477 (May 11, 2001).
Radaeve et al., "Recognition of IgG by Fcy Receptor," *Journal of Biological Chemistry*, vol. 276, No. 19, pp. 16478-16483 (May 11, 2001).
Krapp et al., "Structural Analysis of Human IgG-Fc Glycoforms Reveals a Correlation Between Glycosylation and Structural Integrity," *Journal of Molecular Biology*, vol. 325, pp. 979-989 (2003).
Umaña et al., "Engineered glycoforms of an antineuro-blastoma IgG1 with optimized antibody-dependent cellular cytotoxic activity," *Nature Biotechnology*, vol. 17, pp. 176-180 (Feb. 1999).
Morita et al., "Rpf2p, an Evolutionarily Conserved Protein, Interacts with Ribosomal Protein L11 and Is Essential for the Processing of 27 SB Pre-rRNA to 25 S rRna and the 60 S Ribosomal Subunit Assembly in *Saccharomyces cerevisiae*," *Journal of Biological Chemistry*, vol. 277, No. 32, pp. 28780-28786 (Aug. 9, 2002).
Amigorena et al., "Cytoplasmic Domain Heterogeneity and Functions of IgG Fc Receptors in B Lymphocytes," *Science*, vol. 256, pp. 1808-1812 (Jun. 26, 1992).
Mimura et al., "Role of Oligosaccharide Residues of IgG1-Fc in FcyRIIb Binding," *Journal of Biological Chemistry*, vol. 276, No. 49, pp. 45539-45547 (Dec. 7, 2001).

(Continued)

Primary Examiner—Ilia Ouspenski
(74) Attorney, Agent, or Firm—Foley & Lardner LLP

(57) ABSTRACT

The present invention relates to a method for the production and the selection of human or chimæric or humanized antibodies or molecules that comprise the Fc region of human IgG, capable of modulating the activity of one or several particular Fc receptors, such as the triggering of inhibitory functions through the human type IIB receptors of IgG (FcgammaRIIB/CD32).

13 Claims, 12 Drawing Sheets

OTHER PUBLICATIONS

Figure 3:
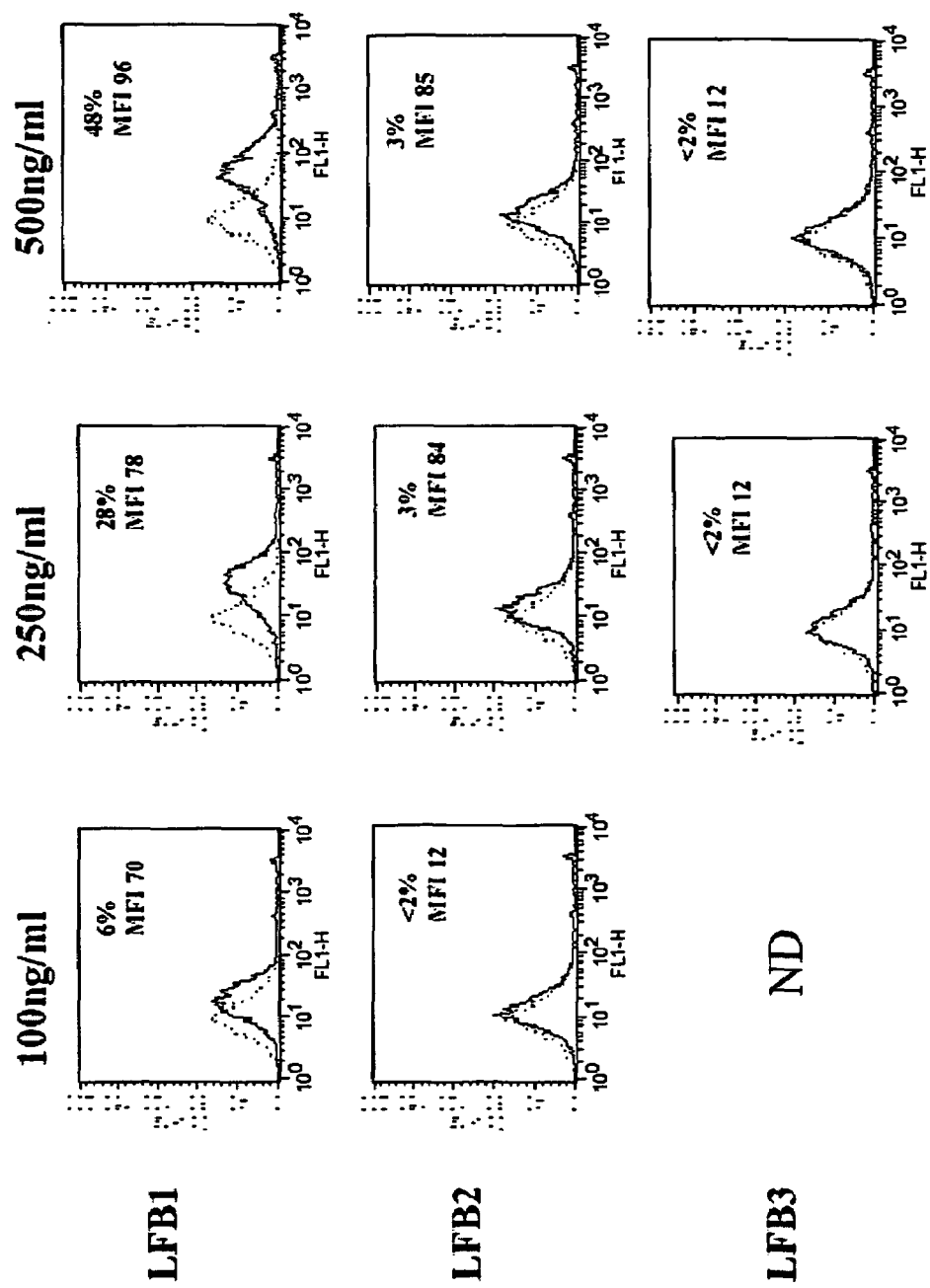

Kato et al., "Structural Basis of the Interaction between IgG and Fcγ Receptors," *Journal of Molecular Biology*, vol. 295, pp. 213-224 (2001).

Lund et al., "Oligosaccharide-protein interactions in IgG can modulate recognition by Fcγ receptors," *The FASEB Journal*, vol. 9, pp. 115-119 (Jan. 1995).

Jefferis et al., "Recognition sites on human IgG for Fcγ receptors: the role of glycosylation," *Immunology Letters*, vol. 44, pp. 111-117 (1995).

Jones et al., "Different Phenotypic Variants of the Mouse B Cell Tumor A20/2J are Selected by Antigen- and Mitogen-Triggered Cytotoxicity of L3T4-Positive, I-A Restricted T Cell Clones," *Journal of Immunology*, vol. 136, No. 1, pp. 348-356 (Jan. 1, 1986).

Malbec et al., "Negative Regulation of Hematopoietic Cell Activation and Proliferation by FcγRIIB," *Immunoreceptor Tyrosine-Based Inhibition Motifs*, M. Daëron and E. Vivier eds., Springer-Verlag, Berlin, Germany, pp. 13-27 (1999).

\* cited by examiner

| Name | Retention time (min) | Area | % Area |
|---|---|---|---|
| Peak 1 | 28.300 | 72387414 | 99.04 |
| *Peak 2* | 45.267 | 700356 | 0.96 |

LFB1 monoclonal antibody is composed of 99% of monomers (Peak 1).

FIGURE 1

| LFB1 | |
|---|---|
| Structure (%) | HPCE-LIF |
| Sialylated | 0.00 |
| Mono-sialylated | 0.00 |
| Bi-sialylated | 0.00 |
| Tri-sialylated | ND |
| Bissecting | 0.00 |
| Fucosylated | 34.95 |
| M3N2 | 0.00 |
| M3N2F | 0.00 |
| G2FB | 0.00 |
| G2F | 6.63 |
| G2B | 0.00 |
| G2 | 8.43 |
| G1FB | 0.00 |
| G1F | 21.37 |
| G1(1,3)FB | 0.00 |
| G1(1,6)FB | 0.00 |
| G1(1,3)F | 3.67 |
| G1(1,6)F | 17.70 |
| G1B | 0.00 |
| G1 | 32.93 |
| G1(1,3)B | 0.00 |
| G1(1,6)B | 0.00 |
| G1(1,3) | 8.29 |
| G1(1,6) | 24.54 |
| G0FB | 0.00 |
| G0F | 6.95 |
| G0B | 0.00 |
| G0 | 26.83 |
| MAN-5 | 0.00 |

ND : Not done

| LFB2 | |
|---|---|
| Structure (%) | HPCE-LIF |
| Sialylated | 0.00 |
| Mono-sialylated | 0.00 |
| Bi-sialylated | 0.00 |
| Tri-sialylated | ND |
| Bissecting | 0.00 |
| Fucosylated | 91.39 |
| M3N2 | 0.00 |
| M3N2F | 0.00 |
| G2FB | 0.00 |
| G2F | 10.04 |
| G2B | 0.00 |
| G2 | 0.00 |
| G1FB | 0.00 |
| G1F | 47.14 |
| G1(1,3)FB | 0.00 |
| G1(1,6)FB | 0.00 |
| G1(1,3)F | 11.68 |
| G1(1,6)F | 35.46 |
| G1B | 0.00 |
| G1 | 4.86 |
| G1(1,3)B | 0.00 |
| G1(1,6)B | 0.00 |
| G1(1,3) | 0.00 |
| G1(1,6) | 4.86 |
| G0FB | 0.00 |
| G0F | 34.21 |
| G0B | 0.00 |
| G0 | 4.61 |
| MAN-5 | 0.00 |

| LFB3 | | |
|---|---|---|
| Structure (%) | HPCE-LIF | HPLC-Fluo* |
| Sialylated | | 46.99 |
| Mono-sialylated | | 40.30 |
| Bi-sialylated | | 6.69 |
| Tri-sialylated | | 0.00 |
| Bissecting | | 0.00 |
| Fucosylated | 68.16 | 0.00 |
| G2F | 54.08 | 0.00 |
| G1 | 4.06 | 0.00 |
| G1F | 22.40 | 0.00 |
| G1(1,3)F | 1.12 | |
| G1(1,6)F | 21.27 | 0.00 |
| G1 | 1.99 | |
| G1(1,3) | 1.00 | |
| G1(1,6) | 0.99 | |
| G0F | 1.69 | 0.00 |
| G0 | 1.18 | 0.00 |
| M3N2F | 0.00 | 0.00 |
| G3F | 0.00 | 0.00 |
| M3N2-G1 | 0.00 | 0.00 |
| M3N2F-G1 | 0.00 | ND |

*Data HPCE-LIF from 1/4 N Ac treated sample.

Different forms of glycans
G0 : ngalactosylated
G1 : monogalactosylated
G2 : bigalactosylated
F : Fucosylated
B : bisecting GlNAc
M3N2 : 3 Man 2 GlNAc

FIGURE 2

| Antibody | Glycosylation (%) | | | RFcγIIIA | | | RFcγIIA | | | RFcγIIIB | | |
|---|---|---|---|---|---|---|---|---|---|---|---|---|
| | Fucose | Galactose | Sialylation | Concentration for inhibition (µM): | | | Concentration for inhibition (µM): | | | Concentration for inhibition (µM): | | |
| | | | | 10% | 30% | 50% | 10% | 30% | 50% | 10% | 30% | 50% |
| Class I | | | | | | | | | | | | |
| LFB1 | 34.95 | 69.36 | 0 | 6x10⁻³ | 0,01 | 0,02 | 0,1 | 0,4 | 0,85 | 0,3 | 0,6 | 1 |
| Class II | | | | | | | | | | | | |
| LFB2 | 91,39 | 62,04 | 0 | 0,09 | 0,1 | 0,2 | 0,2 | 1,2 | NC (>2µM) | 0,6 | NC (>2µM) | NC (>2µM) |
| Rituximab | ND | ND | ND | 0,2 | 1 | 2 | 0,2 | 3,3 | NC (>6µM) | 0,6 | NC (>6µM) | NC (>6µM) |
| Class III | | | | | | | | | | | | |
| LFB3 | 88,16 | 92,52 | 46,99 | 2 | NC (>6µM) | NC (>6µM) | 1,7 | NC (>6µM) | NC (>6µM) | 4 | NC (>6µM) | NC (>6µM) |

ND : Not Done ; NC : Not Calculable (Concentration is not calculable as the indicated percent of inhibition is not found at the highest tested concentration)

FIGURE 9

SEQUENCE LISTING

```
<160> NUMBER OF SEQ ID NOS: 6

<210> SEQ ID NO 1
<211> LENGTH: 21
<212> TYPE: DNA
<213> ORGANISM: artificial
<220> FEATURE:
<223> OTHER INFORMATION: Amplimer sense

<400> SEQUENCE: 1
gcagctcccc caaaggctgt g                                       21

<210> SEQ ID NO 2
<211> LENGTH: 21
<212> TYPE: DNA
<213> ORGANISM: artificial
<220> FEATURE:
<223> OTHER INFORMATION: Amplimer antisense

<400> SEQUENCE: 2
ttggacagtg atggtcacag g                                       21
```

<210> SEQ ID NO 3
<211> LENGTH: 33
<212> TYPE: DNA
<213> ORGANISM: artificial
<220> FEATURE:
<223> OTHER INFORMATION: Amplimer sense

<400> SEQUENCE: 3
tggatgaatt ccctattaag tgatggtgat gtt                                    33

<210> SEQ ID NO 4
<211> LENGTH: 23
<212> TYPE: DNA
<213> ORGANISM: artificial
<220> FEATURE:
<223> OTHER INFORMATION: Amplimer antisense

<400> SEQUENCE: 4
atcggatccc gactgaagat ctc                                               23

<210> SEQ ID NO 5
<211> LENGTH: 990
<212> TYPE: DNA
<213> ORGANISM: human
<220> FEATURE:
<223> OTHER INFORMATION: Constant region of the heavy chain of LFB1/LFB2
      antibody.

<400> SEQUENCE: 5
gcctccacca agggcccatc ggtcttcccc ctggcaccct cctccaagag cacctctggg        60
ggcacagcgg ccctgggctg cctggtcaag gactacttcc ccgaaccggt gacggtgtcg       120
tggaactcag gcgccctgac cagcggcgtg cacaccttcc cggctgtcct acagtcctca       180
ggactctact ccctcagcag cgtggtgacc gtgccctcca gcagcttggg cacccagacc       240
tacatctgca acgtgaatca caagcccagc aacaccaagg tggacaagaa agttgagccc       300
aaatcttgtg acaaaactca cacatgccca ccgtgcccag cacctgaact cctggggggga      360 ccgtcagtct tcctcttccc cccaaaaccc aaggacaccc tcatgatctc ccggacccct       420
gaggtcacat gcgtggtggt ggacgtgagc cacgaagacc ctgaggtcaa gttcaactgg       480
tacgtggacg gcgtggaggt gcataatgcc aagacaaagc cgcgggagga gcagtacaac       540
agcacgtacc gtgtggtcag cgtcctcacc gtcctgcacc aggactggct gaatggcaag       600
gagtacaagt gcaaggtctc caacaaagcc ctcccagccc ccatcgagaa aaccatctcc       660
aaagccaaag ggcagccccg agaaccacag gtgtacaccc tgcccccatc ccgggatgag       720
ctgaccaaga accaggtcag cctgacctgc ctggtcaaag gcttctatcc cagcgacatc       780
gccgtggagt gggagagcaa tgggcagccg gagaacaact acaagaccac gcctcccgtg       840
ctggactccg acggctcctt cttcctctac agcaagctca ccgtggacaa gagcaggtgg       900
cagcagggga acgtcttctc atgctccgtg atgcatgagg ctctgcacaa ccactacacg       960
cagaagagcc tctccctgtc tccgggtaaa                                        990

<210> SEQ ID NO 6
<211> LENGTH: 990
<212> TYPE: DNA
<213> ORGANISM: human
<220> FEATURE:
<223> OTHER INFORMATION: Constant region of the heavy chain of LFB3
      antibody.

<400> SEQUENCE: 6

```
                                    -continued gcctccacca agggcccatc ggtcttcccc ctggcaccct cctccaagag cacctctggg        60
ggcacagcgg ccctgggctg cctggtcaag gactacttcc ccgaaccggt gacggtgtcg       120
tggaactcag gcgccctgac cagcggcgtg cacaccttcc cggctgtcct acagtcctca       180
ggactctact ccctcagcag cgtggtgacc gtgccctcca gcagcttggg cacccagacc       240
tacatctgca acgtgaatca caagcccagc aacaccaagg tggacaagag agttgagccc       300
aaatcttgtg acaaaactca cacatgccca ccgtgcccag cacctgaact cctgggggga       360
ccgtcagtct tcctcttccc cccaaaaccc aaggacaccc tcatgatctc ccggacccct       420
gaggtcacat gcgtggtggt ggacgtgagc cacgaagacc ctgaggtcaa gttcaactgg       480
tacgtggacg gcgtggaggt gcataatgcc aagacaaagc cgcgggagga gcagtacaac       540
agcacgtacc gtgtggtcag cgtcctcacc gtcctgcacc aggactggct gaatggcaag       600
gagtacaagt gcaaggtctc caacaaagcc ctcccagccc ccatcgagaa aaccatctcc       660
aaagccaaag gcagccccg agaaccacag gtgtacaccc tgcccccatc ccgggaggag        720
atgaccaaga accaggtcag cctgacctgc ctggtcaaag gcttctatcc cagcgacatc       780
gccgtggagt gggagagcaa tgggcagccg gagaacaact acaagaccac gcctcccgtg       840
ctggactccg acggctcctt cttcctctat agcaagctca ccgtggacaa gagcaggtgg       900
cagcagggga acgtcttctc atgctccgtg atgcatgagg ctctgcacaa ccactacacg       960
cagaagagcc tctccctgtc cccgggtaaa                                       990
```

PREPARATION OF HUMAN, HUMANIZED OR CHIMAERIC ANTIBODIES OR POLYPEPTIDES HAVING DIFFERENT BINDING PROFILES TO FCGAMMA RECEPTORS

The present invention relates to a method for the production and the selection of human or chimæric or humanized antibodies or molecules that comprise the Fc region of human IgG, capable of modulating the activity of one or several particular Fc receptors, such as the triggering of inhibitory functions through the human type II receptors of IgG (FcgammaRII/CD32).

INTRODUCTION

Antibody based therapy in human has emerged with the possibility of producing partially human antibodies (chimeric antibodies) and more recently humanized antibodies. Humanized or murine/human chimeric recombinant antibodies have been developed to prevent the appearance of human anti-mouse antibodies ("HAMA") in patients treated with mouse antibodies, thus avoiding side-effects due to the formation of immune-complexes between HAMA and the injected antibody. In addition, such engineered antibodies exhibit stronger effector functions than their murine counterparts, as their binding to human FcgammaR is improved. Numerous antibodies are currently being tested in clinical trials for the treatment of cancer for example. But, as of today, only few antibodies have shown efficacy at low dose and several trials have been prematurely terminated. Higher dose antibody administration is mainly limited by two factors. First, it increases likewise numerous side effects. Second, it is still a problem to produce large quantities of antibodies and the cost associated with scaling-up is not always economically viable.

These problems need to be addressed before applying antibodies therapy to large population afflicted with various diseases.

It has been shown that the Fc region of IgG is essential for the functions of antibodies. The recruitment of C1q and of membrane FcgammaR through the Fc region of IgG allows to trigger various effector mechanisms such as cytotoxicity, cytokine release or endocytosis. For instance, it has been shown that human IgG1, the most represented human IgG subclasses, that comprise IgG1, IgG2, IgG3 and IgG4, triggers the highest antibody-dependent cell cytotoxicity (ADCC). It is due to the ability of human IgG1 to efficiently bind to FcgammaR expressed on NK cells and monocytes/macrophages. In addition, FcgammaR play an important role in immune regulation by triggering inhibitory functions.

Three distinct classes of FcgammaR have been defined both in humans and mice. Human FcgammaR include the high affinity FcgammaRI (CD64), and the low-affinity FcgammaR, FcgammaRII (CD32) and FcgammaRIII (CD16). Three genes encode FcgammaRI isoforms (A, B, C), three genes encode FcgammaRII isoforms (A1, B1, B2) and two genes encode FcgammaRIII isoforms (A, B). Attempts have been made to improve the efficacy of IgG antibodies by modifying the amino-acid sequence in the Fc domain so that a modulation of the interactions of Fc region with FcgammaR can be achieved (see for example WO 99/54572).

Biophysical and molecular studies have indicated that several amino-acid residues located in the hinge region between the CH1 and CH2 domains and immediately adjacent to the N-terminus of the CH2 domain of IgG1, as well as the sugar chain linked to the CH2 domain at position $Asn^{297}$, play a critical role in FcgammaR binding. On the one hand, a common set of IgG1 residues is involved in binding to all FcgammaR (I, II, III), but residues outside this common set were identified when FcgammaRII and FcgammaRIII interactions with human Fcgamma1 were studied in details (Shields et al., J. Biol. Chem., 276, 6591-6604, 2001). On the other hand, although not in direct contact with the FcgammaR, the carbohydrate attached to the conserved residue $Asn^{297}$ on Fc is likely to stabilize the conformation of the receptor binding epitope on Fc (Radaev et al., J. Biol. Chem., 276, 16469-16477, 2001). It has been hypothesized that deglycosylation causes a conformational change in the relative orientation of the two CH2 domains such as the Fc transitions from an open to a closed conformation, preventing FcgammaR binding (Radaev & Sun, J. Biol. Chem., 276, 16478-16483, 2001). Analysis of IgG1 glycoforms bearing consecutively truncated oligosaccharides confirmed that removal of sugar residues permits the mutual approach of CH2 domains resulting in the generation of a closed conformation (Krapp et al., J. Mol. Biol., 325, 979-989, 2003).

Engineered IgG glycoforms have been shown to trigger optimized ADCC through the recruitment of FcgammaRIII. First, Umana et al. proposed that an IgG1 antibody engineered to contain increasing amounts of bisected complex oligosaccharides (bisecting N-acetylglucosamine, GlcNAC) would allow to trigger a strong ADCC as compared to its parental counterpart (Umana et al., Nature Biotechnol., 17, 176-180, 1999), although this claim has been challenged (Shinkawa et al., J. Biol. Chem, 2002).

Such contradictory results show that it is difficult to identify the actual optimized oligosaccharides structures responsible for the activation or inhibition of a given FcR We found that it is more relevant to identify patterns involved in improved binding rather than focusing on a unique structure. Indeed, we have observed that binding occurs within a range of similar structures.

In this regard, we have demonstrated that particular glycosylation patterns attached to the Fc domain are responsible for enhancing Fc region—FcRIII receptors interaction. In this regard, we filed WO 01/77181 showing that it is possible to prepare compositions of antibodies with improved ADCC properties from particular cell lines, such as YB2/0, and demonstrating the role of particular glycosylation patterns. Such antibodies present short oligosaccharide chains, a weak sialylation, no or weak level of bisecting GlcNac and a low level of fucose between 20% and 50%.

It was also postulated in WO 00/61739 that the presence or the absence of fucose modulates the activity of antibodies. The lack of fucose on human IgG1 N-linked oligosaccharides has been shown to improve FcgammaRIII binding and ADCC. Recombinant human IgG1 produced in YB2/0 cells (Shinkawa et. al., J. Biol. Chem., 2002) or in CHO-Lec13 cells (Shields et al., J. Biol. Chem., 277, 26733-26740, 2002), which exhibited a low-fucose content or were deficient in fucose as compared to the same IgG1 produced in wild-type CHO cells, showed an enhanced ability to trigger cellular cytotoxicity. By contrast, a correlation between galactose and ADCC was not observed and the content of bisecting GlcNAC only marginally affected ADCC (Shinkawa et al., J. Biol. Chem., 2002).

While the above results confirm what we previously described in our application WO 01/77181, we now have evidence showing that the alteration of antibody activity can not be resumed solely at the fucose level. The implication of GlcNac, mannose, sialic acid, galactose and their respective position is extremely variable in antibodies produced from different cell lines. This observation confirms that different glycosylation patterns are not only involved in Fc region—Fc receptors interaction but are also responsible for the function of the antibody.

Therefore, the general purpose of the invention is to provide a method for fine-tuning the function of a given antibody in respect to the different Fc receptors. Different defined patterns would allow the modulation of the different FcR.

Among the receptors for the Fc region of IgG, type IIB Fcgamma receptors is of particular interest. FcRII are single-chain, low-affinity receptors that bind with increased affinity IgG present in immune-complexes or bound to cell surface antigens. Genetic and protein analyses have shown that FcgammaRIIB are present under two isoforms in Humans (FcgammaRIIB1 and FcgammaRIIB2), generated by alternative splicing of the three exons that encode the intracytoplasmic domain of the receptor. FcgammaRIIB are expressed on B cells, monocytes, dendritic cells, mast cells and basophils. By contrast to all the other known FcgammaR, FcgammaRIIB isoforms inhibit cell activation induced through activating receptors (Amigorena et al., Science, 256, 1808-1812, 1992). Molecular analyses have shown that the presence of an YxxL motif, termed "immunoreceptor tyrosine-based inhibition motif" (ITIM) in the intracellular domain of FcgammaRIIB is directly involved in the inhibitory function of the receptor. When tyrosyl phosphorylated, ITIM binds SH2 domain of phosphatases, namely SHP-1, SHP-2 and the phosphatidylinositol polyphosphate 5-phosphatase, SHIP. SHIP can dephosphorylate PIP3 into PI(3,4)P2, preventing the recruitment of the kinase btk which phosphorylates phospholipase C-gamma (PLC gamma). The production of inositol (1,4,5)-tri-phosphate (IP3) is then blocked. It leads to the inhibition of the influx of extracellular calcium, an early event triggered by the recruitment of activating receptors. It also inhibits late events such as cytokine production or cell proliferation (reviewed in O. Malbec et al., in "Immunoreceptor Tyrosine-based Inhibition Motifs", M. Daëron & E. Vivier eds, 1999, Springer-Verlag, Berlin, pp. 13-27).

The biological significance of FcgammaRII-dependent negative regulation has been examined by a number of authors. It has been shown that negative regulation of antibody responses can be achieved through the recruitment of FcgammaRIIB, although it is likely that other mechanisms concur in the negative regulation of antibody responses. Thus, one can suggest that antibody-based auto-immune diseases or unwanted allo-immunization leading to the appearance of pathogenic antibodies could be circumvented through an optimized recruitment of FcgammaRIIB by antibodies or other molecules capable of binding to FcgammaRIIB.

In addition, the recruitment of FcgammaRIIB present on mast cells and basophils by allergen-complexed IgG and the subsequent co-aggregation of FcgammaRIIB with FcepsilonRI, once IgE are complexed to the same allergen, is responsible for the blockade of the anaphylactic response by these cells. Thus, IgG antibodies with an optimized ability to engage FcgammaRIIB and, hence, to trigger FcgammaRIIB inhibitory functions could represent efficient therapeutic tools in the treatment of allergy.

Finally, the inhibitory functions triggered by the recruitment of FcgammaRIIB could be exploited in cancer patients. On the one hand, it has been shown that FcgammaRIIB K.O. mice exhibit better anti-tumor responses in models where immuno-deficient FcgammaRIIB$^{-/-}$ mice were tumor-engrafted and treated with recombinant monoclonal antibodies such as anti-CD20 or anti-HER2/Neu chimæric or humanized antibodies, respectively. Thus, monoclonal IgG antibodies unable to trigger strong FcgammaRII inhibitory functions might represent optimized tools in tumor treatments. On the other hand, FcgammaRIIB negatively regulate hematopoietic cell proliferation dependent on Receptor Tyrosine Kinases (RTKs). Bifunctional molecules such as anti-RTK IgG antibodies with optimized Fc region capable of efficiently co-aggregating RTKs with FcgammaRIIB could therefore block the proliferation of FcgammaRIIB$^+$ tumor cells.

The impact of glycosylation on FcgammaRII/human IgG interaction has also been documented using soluble FcgammaR ectodomains. Both for mouse FcgammaRII and human FcgammaRIIB, a 1:1 stoichiometry has been deduced from sedimentation equilibrium technique with ultracentrifugation and isothermal titration calorimetry (ITC), respectively (Mimura et al., J. Biol. Chem., 276, 45539-45547, 2001; Kato et al., J. Mol. Biol., 295, 213-224, 2001). Interactions between Asn$^{297}$ and the primary GlcNAC residue were shown to be important for recognition of human chimeric IgG3 by human FcgammaRII (Lund et al., FASEB J., 116, 115-119, 1995). Replacement of contact residues for galactose on the alpha(1-6) mannose arm does not affect FcgammaRII recognition while replacement of Asp$^{265}$, a contact for a core GlcNAC residue, results in a loss of Fc gammaRII recognition (Jefferis et al., Immunol. Letters, 44, 111-117, 1995). In addition, another study indicated that GlcNAC residues contribute only slightly to receptor binding of human IgG1, whereas removal of alpha(1-3)- and alpha(1-6)-arm mannose residues results in a significantly decreased affinity (Mimura et al., J. Biol. Chem., 276, 45539-45547, 2001). The same study concluded that the truncation of oligosaccharides causes a closed disposition of the two CH2 domains and is accompanied by a decreased binding to FcgammaIIB. By contrast to FcgammaRIII, antibodies produced in CHO-Lec13 cells, thus devoided of fucose, showed only a slight improvement in binding to the soluble immobilized Arg$^{131}$-FcgammaRIIA polymorphic form and to the soluble FcgammaRIIB form, and none to the soluble His$^{131}$-FcgammaRIIA polymorphic form (both of them corresponding to the extracellular and transmembrane domains). Since the former receptors have arginine at position 131, it was postulated that the fucose may interact directly with the FcRgammaII residue at this position or alter the IgG1 conformation so that a slight negative effect on FcgammaRII binding is induced by its presence (Shields et al., J. Biol. Chem., 277, 26733-26740, 2002). The same study suggested that the galactose content does not affect binding to FcgammaRII.

Herein, we propose to prepare different classes of antibodies that present different binding profiles, so as to produce drugs that can be fine-tuned depending on targets and diseases. The method of preparation of such antibodies allows for the first time to identify suitable cell lines for producing antibodies with enhanced efficacy, and/or with enhanced immuno-modulatory functions and specificity for FcgammaRs. The invention also provides the glycanic structure of the antibodies responsible for their specific binding profile, as well as methods for producing such specific antibodies.

DISCLOSURE OF THE INVENTION

The present invention provides a method for producing and selecting human recombinant antibodies or chimæric antibodies or humanized antibodies or molecules that comprise Fc region of human IgG with defined glycosylation patterns by binding assays—immunofluorescence—that use different FcRs, in particular FcgammaRIIB, FcgammaRIIA, and FcgammaRIIIA. For example, this method can be applied for selecting human recombinant antibodies or antibody-derived molecules with defined glycosylation patterns, capable of specifically triggering inhibitory functions through the human type IIB receptors for the Fc region of IgG (FcgammaRIIB/CD32B) by functional assays such as calcium mobilization assay and cytokine secretion assay.

The invention is based on the production of recombinant human, humanized or chimæric antibodies with different Fc glycosylation patterns by various cell lines cultured in defined media leading to specialized and fine-tuned antibodies.

More specifically, the present invention relates to the production and selection of antibodies with specific structural characteristics determined by different Fc glycosylation patterns allowing them to turn on or to turn off the negative regulation exerted by FcgammaRIIB on FcgammaRIIB+ cells (i.e. cells expressing FcgammaRIIB), such as B cells, monocytes or other antigen-presenting cells (APC), mast cells, basophils, or any other FcgammaRIIB+ cells such as transformed and tumor cells.

The present invention relates to optimized antibodies that will be useful therapeutic tools for controlling antibody responses. It allows to produce and to select antibodies of any specificities or other molecules optimized for binding to FcgammaRIIB, capable of triggering immuno-modulatory inhibitory functions through the recruitment of FcgammaRIIB in antibody-based auto-immune diseases or in unwanted alloimmunization leading to the appearance of pathogenic antibodies, notably against infused recombinant antibodies.

The present invention relates to optimized antibodies of any specificities that will be useful therapeutic tools for controlling antibody efficacy in antibody-based treatments. It allows to produce and select antibodies with weak or no FcgammaRIIB binding, thus preventing the triggering of immunomodulatory inhibitory functions through FcgammaRIIB during antibody-based therapeutic treatments such as cancer treatments with therapeutic anti-tumor antibodies.

In a first aspect, the invention is directed to a method for the preparation of human, humanized or chimæric antibodies or polypeptides comprising Fc region of human IgG, said antibodies or polypeptides having different binding profiles, wherein said method comprises the steps consisting of:
a) providing candidate human, humanized or chimæric antibodies or polypeptides comprising Fc region of human IgG produced naturally by or following transfection with a vector comprising the coding sequence for said antibody or polypeptide of cells from animal cell lines comprising hybridoma, heterohybridoma, EBV-transformed human B cell lines or from eukaryotic microorganisms,
b) testing the binding of said antibodies or polypeptides on Fcgamma receptors including FcgammaRIIIA, FcgammaRIIA and FcgammaRIIB,
c) selecting antibodies or polypeptides which:
i) bind to both FcgammaRIIIA, FcgammaRIIA and FcgammaRIIB, or
ii) bind to both FcgammaRIIA and FcgammaRIIB but do not bind or bind only weakly to FcgammaRIIIA, or
iii) do not bind or bind only weakly to both FcgammaRIIIA, FcgammaRIIA and FcgammaRIIB.

The binding of these antibodies to FcgammaRIIIA, FcgammaRIIA, and FcgammaRIIB is through their constant region (that is, CH1, CH2, CH3), more specifically through their Fc region. These antibodies can exhibit any kind of specificity through their variable regions, i.e. through their antigen-binding region or through their complementarity-determining regions (CDRs).

The antibodies prepared by the means defined herein belong to one of three classes, each one having particular binding profile, and consequently different properties, allowing to use each class for a particular, well-defined therapeutic goal.

The antibodies or polypeptides belonging to the first class, can be prepared using the step c) i) of the above method. Because they are able to bind to FcgammaRIIIA, they are able to induce ADCC through this receptor. In addition, because they are able to bind FcgammaRIIA, they are able to induce ADCC and phagocytosis through FcgammaRIIA positive monocytes and macrophages. Furthermore, this class of antibodies or polypeptides is also able to trigger inhibitory functions through the FcgammaRIIB, to which they are able to bind. These antibodies are therefore able to exert immunomodulatory functions through FcgammaRIIB. It relates to the capacity of such antibodies to negatively immunoregulate cells from the immune system or tumor cells. Such a capacity is of major importance in a number of diseases and in various clinical situations such as transplantation, allo-immunization or antibody-based treatments.

Thus, the antibodies or polypeptides belonging to this class are both highly cytotoxic antibodies (or polypeptides) and potent immunomodulatory antibodies (or polypeptides).

The second class of antibodies or polypeptides can be prepared using step c) ii) of the above method. They are of interest because they are only poorly cytotoxic as compared to the antibodies belonging to the first class, due to their weaker binding to FcgammaRIII, and notably FcgammaRIIIA. More particularly, they are not cytotoxic in presence of polyclonal polyvalent IgG (intravenous IgG, IVIg). They are able to induce ADCC and phagocytosis through FcgammaRIIA positive monocytes and macrophages due to their ability to bind FcgammaRIIA. In addition, they are immunomodulatory antibodies due to their ability to bind FcgammaRIIB.

Finally, the third class of antibodies may be prepared using step c) iii) of the above method. This class of antibodies is not cytotoxic, and does not provide any immuno-immuno-modulatory activity. More specifically, they are not cytotoxic in presence of polyclonal polyvalent IgG (intravenous IgG, IVIg). They are of interest because they can be used in vivo without triggering effector functions achieved through FcgammaR recruitment, due to their inability to bind or weak binding to FcgammaRIIIA, FcgammaRIIA, and FcgammaRIIB.

Thanks to the method according to the invention, it is now possible to prepare antibodies with a specific or desired therapeutic profile, depending on which FcgammaR (IIIA, IIA, IIB) is targeted.

Advantageously, the method according to the invention is based on a competition assay using monomeric antibodies as competitors.

The competition assay can use monomeric antibodies as competitors is an immunofluorescence competition assay.

In another embodiment, the competition assay can use monomeric antibodies as competitors is a direct or indirect immunofluorescence competition assay.

In this assay, the ID50 is the dose of the tested antibody (expressed in microM), that leads to a 50% decrease of stained FcgammaR positive indicator cells with a referenced anti-FcgammaR antibody coupled to a fluorochrome.

In this assay, the ID30 is the dose of the tested antibody (expressed in microM), that leads to a 30% decrease of stained FcgammaR positive indicator cells with a referenced anti-FcgammaR antibody coupled to a fluorochrome.

In this assay, the ID10 is the dose of the tested antibody (expressed in microM), that leads to a 10% decrease of stained FcgammaR positive indicator cells with a referenced anti-FcgammaR antibody coupled to a fluorochrome.

The expression "bind to" means that the antibodies under monomeric form bind to FcgammaRIIIA with an ID50 inferior to 0.2 microM, or an ID50 inferior to 0.1 microM, advantageously inferior to 0.05 microM, and much more advantageously inferior or equal to 0.02 microM in a competition assay with the mouse monoclonal antibody fluorochrome-labelled 3G8. 3G8 is an antibody directed against FcgammaRIII, and well known of the state of the art (3G8-PE, Immunotech, France, Cat N° A07766).

The expression "bind to" means that the antibodies under monomeric form bind to FcgammaRIIA with an ID50 inferior to 6 microM, or an ID50 inferior to 2 microM, advantageously inferior to 1 microM, and much more advantageously inferior or equal to 0.85 microM in a competition assay with the mouse monoclonal antibody fluorochrome-labelled AT10. AT10 is an antibody directed against FcgammaRIIA and FcgammaRIIB, and well known of the state of the art (AT10-FITC, Serotec, Cat N° MCA 1075F).

The expression "bind to" means that the antibodies under monomeric form bind to FcgammaRIIB with an ID50 inferior to 6 microM, or more advantageously inferior to 2 microM, and much more advantageously inferior to 1 microM in a competition assay with the mouse monoclonal antibody fluorochrome-labelled AT10. AT10 is an antibody specific of FcgammaRIIA and FcgammaRIIB, and well known of the state of the art (AT10-FITC, Serotec, United Kingdom, Cat N° MCA 1075F).

The expression "do not bind or bind only weakly" means that the antibodies under monomeric form bind to FcgammaRIIIA with an ID50 superior or equal to 0.2 microM, advantageously superior to 0.5 microM, more advantageously superior to 1 microM or superior to 2 microM, and the most advantageously superior to 10 microM in a competition assay with the mouse monoclonal antibody fluorochrome-labelled 3G8.

The expression "do not bind or bind only weakly" means that the antibodies under monomeric form bind to FcgammaRIIA with an ID50 superior or equal to 6 microM, advantageously superior to 9 microM, more advantageously superior to 15 microM or superior to 20 microM, and the most advantageously superior to 50 microM in a competition assay with the mouse monoclonal antibody fluorochrome-labelled AT10.

The expression "do not bind or bind only weakly" means that the antibodies under monomeric form bind to FcgammaRIIB with an ID50 superior or equal to 6 microM, advantageously superior to 9 microM, more advantageously superior to 15 microM or superior to 20 microM, and the most advantageously superior to 50 microM in a competition assay with the mouse monoclonal antibody fluorochrome-labelled AT10.

Binding to FcgammaRIIIA, to FcgammaRIIA, and to FcgammaRIIB as used herein refers to a binding of antibodies where only a low percentage of aggregates is present in antibody preparation (<2%), and where antibodies are not complexed on purpose by any mean such as heat or chemical aggregation or by formation of immune-complexes with the relevant antigen or with F(ab')2 anti-human IgG.

In another embodiment, the method is based on a binding assay using complexed antibodies.

The binding assay can be an immunofluorescence binding assay using complexed antibodies.

Advantageously, the binding assay is a direct or indirect immunofluorescence binding assay using complexed antibodies.

Binding to FcgammaRIIIA, FcgammaRIIA, and to FcgammaRIIB as used herein refers to a binding of antibodies complexed with F(ab)'$_2$ anti-human IgG.

According to the invention, the expression "bind to" in the method that uses an immunofluorescence binding assay with complexed antibodies, means that the antibodies give at least a percentage of 30%, 15%, 5% positive indicator cells in an immunofluorescence assay that measures the binding of complexed antibody (used at 500, 250, and 100 ng/ml, respectively) to FcgammaRIIIA positive indicator cells.

According to the invention, the expression "bind to" in the method that uses an immunofluorescence binding assay with complexed antibodies, means that the antibodies give at least a percentage of 70%, 60%, 30% positive indicator cells in an immunofluorescence assay that measures the binding of antibody (used at 10, 5, and 1 microg/ml, respectively) to FcgammaRIIA positive indicator cells.

According to the invention, the expression "bind to" in the method that uses an immunofluorescence binding assay with complexed antibodies, means that the antibodies give at least a percentage of 50%, 25% positive indicator cells in an immunofluorescence assay that measures the binding of antibody (used at 50, and 25 microg/ml, respectively) to FcgammaRIIB positive indicator cells.

The expression "do not bind or bind only weakly" in the method that uses an immunofluorescence binding assay with complexed antibodies means that the antibodies give a percentage lower than 30%, 15%, 5% of positive indicator cells in an immunofluorescence assay that measures the binding of complexed antibody (used at 500, 250, and 100 ng/ml, respectively) to FcgammaRIIIA positive indicator cells.

The expression "do not bind or bind only weakly" in the method that uses an immunofluorescence binding assay with complexed antibodies means that the antibodies give a percentage lower than 70%, 60%, 30% of positive indicator cells in an immunofluorescence assay that measures the binding of antibody (used at 10, 5, and 1 microg/ml, respectively) to FcgammaRIIA positive indicator cells.

The expression "do not bind or bind only weakly" in the method that uses an immunofluorescence binding assay with complexed antibodies means that the antibodies give a percentage lower than 30%, 10% of positive indicator cells in an immunofluorescence assay that measures the binding of antibody (used at 50, and 25 microg/ml, respectively) to FcgammaRIIB positive indicator cells.

Advantageously, the antibodies or polypeptides selected in the step c) i) are produced by cells from lymphoid cell lines or lymphoid-derived cell lines or hybridomas or from epithelial kidney cell lines, the antibodies or polypeptides selected in the step c) ii) are produced by cells from non-lymphoid cell lines and the antibodies or polypeptides selected in the step c) iii) are produced by cells from an heterohybridoma fused to cells from an EBV-transformed cell line or to B lymphocytes from human donors.

The term "lymphoid cell lines" refers to cells cultured in long-term in vitro cultures, derived from human lymphocytes by any mean. Specifically, such cell lines can be obtained by EBV transformation. The term "lymphoid-derived cell lines" refers to cells derived from lymphoid cell lines by any mean such as fusion of cells from a lymphoid cell line with partner cells. Such partner cells may be B lymphocytes derived from human donors. The term "hybridoma" refers to cells derived from the fusion of B cells with myeloma cells. The term "heterohybridoma" refers to cells obtained by fusing cells from a murine myeloma cells with human malignant lymphoid cells from a patient with nodular lymphoma.

As referred herein the identified antibodies or polypeptides encompass the identified cell lines capable of producing antibodies or antibody-derived molecules that display the above relevant features.

In a particular aspect of the invention, the lymphoid-derived cell lines are rat myeloma cell lines or the hybridoma YB2/0 cell line (ATCC number CRL-1662) or cell lines derived thereof, and/or the epithelial kidney cell line is VERO (ATCC number CCL-81), or cell lines derived thereof, and/or the non-lymphoid cell line is CHO (ATCC number CCL-61) or cell lines derived thereof and/or said heterohybridoma is K6H6B5 (ATCC number CRL-1823) or cell lines derived thereof.

CHO cell line can be a CHO dhfr- cell line (Columbia University, New York, USA).

In a preferred embodiment of the invention, the binding assays can be performed using:
i) indicator cells from cell lines that express different Fc receptors on their cell surface,
ii) recombinant Fc receptors comprising FcgammaR ectodomains, Fc receptors derived-peptides.

The indicator cells may be for example Jurkat-CD16 (expressing FcgammaRIIIA), CD32 positive K562 (expressing FcgammaRIIA) (ATCC number CCL-243) or CD32 positive IIA1.6 (expressing FcgammaRIIB).

The term "Fc receptors comprising FcgammaR ectodomains" refers to the extracellular region of the Fcgamma receptors type IIA, IIB and IIIA made of two ectodomains (D1 and D2).

On a preferred embodiment, the subset of antibodies or polypeptides selected for their ability to bind to both FcgammaRIIIA, FcgammaRIIA and FcgammaRIIB, and the subset of antibodies or polypeptides selected for their ability to bind to both FcgammaRIIA and FcgammaRIIB are further tested and selected by functional assays for their ability i) to trigger FcgammaRIIIA leading to improved ADCC, increased production of cytokines such as Interleukin-2 (IL-2) and of pro-inflammatory molecules such as Tumor Necrosis Factor alpha (TNF alpha); and ii) to trigger FcgammaRIIB, leading to the inhibition of calcium mobilization and to the inhibition of cytokine production such as IL-2 by cells expressing FcgammaRIIB such as B cells and monocytes.

Advantageously, the functional assays consist of a calcium mobilization inhibition assay, and/or a cytokine secretion inhibition assay.

An activity of antibodies belonging to the first and the second classes according to the invention includes the inhibition of calcium mobilization, by co-aggregation of such antibodies bound to surface FcgammaRIIB with activating surface receptors such as BCR, TCR, FcepsilonRI. Calcium mobilization as used herein refers to the influx of extracellular calcium into a cell following the recruitment of activating receptors such as BCR.

An activity of antibodies of the present invention includes the inhibition of cytokine production by co-aggregation of such antibodies bound to surface FcgammaRIIB with activating surface molecules such as BCR.

Cytokine production as used herein refers to the release of cytokine by a cell following the recruitment of activating receptors such as BCR.

The inhibition of cytokine production by molecules of the present invention includes inhibition of Interleukin-2 (IL-2) production.

In another embodiment, the functional assays can further comprise a specific FcgammaRIIIA ADCC assay.

Basically, this specific FcgammaRIIIA ADCC assay consists of the addition of each antibody or polypeptide to a distinct reaction mixture comprising target cells, effector cells expressing FcgammaRIIIA and polyvalent IgG, and the determination of target cells lysis percentage.

Another object of the invention is the use of cells from lymphoid cell lines or lymphoid-derived cell lines or hybridoma or from epithelial kidney cell lines to produce antibodies that are able to bind to FcgammaRIIIA, FcgammaRIIA and FcgammaRIIB.

The term "hybridoma" has the same meaning that mentioned above. Advantageously, the hybridoma can be derived from a rat myeloma cell fused to lymphocytes.

The values of ID10, ID30 and ID50 of antibodies produced by YB2/0 hybridoma cells, for their binding to FcgammaRIIIA, FcgammaRIIA and FcgammaRIIB, are summarized in the FIG. 9 and show the strong binding of these antibodies for the three types of receptors.

In a particular embodiment of the invention, the antibodies produced by cells from lymphoid cell lines or lymphoid-derived cell lines or hybridoma or from epithelial kidney cell lines are immunomodulatory antibodies.

The antibodies produced by hybridoma cells, and more particularly by hybridoma cells resulting from B cell fusion with rat myeloma cells are able to bind to FcgammaRIIB, and therefore to trigger inhibition of cell functions through FcgammaRIIB.

According to the invention, the antibodies produced by hybridoma cells, and preferably by hybridoma cells resulting from the fusion of B cells with rat myeloma cells, belong to the first class of antibodies described above. As a result, they can also be selected thanks to the step c) i) of the method described above.

These antibodies produced by cells from lymphoid cell lines or lymphoid-derived cell lines or hybridoma or from epithelial kidney cell lines are both immunomodulatory and cytotoxic antibodies.

These immunomodulatory antibodies produced by hybridoma cells, and preferably by hybridoma cells resulting from the fusion of B cells with rat myeloma cells, are able to bind to FcgammaRIIIA and FcgammaRIIA. These receptors are activator receptors, and trigger cytotoxic activity.

In a preferred embodiment the hybridoma cell line is YB2/0.

In another preferred embodiment, the epithelial kidney cell line is VERO.

Another object of the invention is the use of cells from non-lymphoid cell lines to produce antibodies that do not bind or bind only weakly to FcgammaRIIIA but bind to both FcgammaRIIA and FcgammaIIB.

The applicant shows in the present application that antibodies produced by a non lymphoid cell line bind weakly to FcgammaRIIIA, if not, but bind to FcgammaRIIA and FcgammaIIB. FIG. 9 summarizes the values of ID10, ID30 and ID 50 of antibodies produced by the cell line CHO and shows the weak binding of these antibodies to FcgammaRIIIA, and the binding of these antibodies to FcgammaRIIA and FcgammaRIIB.

These antibodies produced from cells from non-lymphoid cell lines are immunomodulatory antibodies.

This immunomodulatory activity is due to the binding of these antibodies to FcgammaRIIB.

Furthermore, these antibodies produced from non-lymphoid cell lines induce ADCC and phagocytosis by monocytes and macrophages expressing FcgammaRIIA.

These antibodies, that belong to the second class of antibodies described above, may also be prepared or selected thanks to the step c) ii) of the method already described.

In a preferred embodiment, the non-lymphoid cell line is CHO (ATCC number CCL-61).

In another embodiment, CHO cell line can be CHO dhfr- (Columbia University, New York, USA).

Still another object of the invention is the use of cells from an heterohybridoma fused to cells from an EBV-transformed cell line, or to B cells, to produce antibodies that do not bind or bind weakly to both FcgammaRIIIA, FcgammaRIIA and FcgammaRIIB.

The applicant shows in the present application that antibodies produced by a heterohybridoma fused to B cells bind weakly to FcgammaRIIIA, FcgammaRIIA and FcgammaIIB. FIG. 9 summarizes the values of ID10, ID30 and ID 50 of antibodies produced by cells from the heterohybridoma K6H6B5 fused to B cells and shows the weak binding of these antibodies to FcgammaRIIIA, FcgammaRIIA and FcgammaIIB.

Advantageously, these antibodies produced by cells from an heterohybridoma fused to cells from an EBV-transformed cell line, or to B cells are used as therapeutic alternative to the use of IgG4.

IgG4 are used to avoid the recruitment of effector functions through FcgammaRIIIA, FcgammaRIIA, and FcgammaRIIB. The antibodies produced from a heterohybridoma fused to B cells or EBV-transformed B cells according to the invention, belong to the IgG1 isotype. They are of interest because they can be used in vivo without triggering effector functions achieved through FcgammaRIIIA, FcgammaRIIA, FcgammaRIIB recruitment, preventing the development of severe-side effects triggered by FcgammaR and FcepsilonRI binding during the treatment of certain diseases.

In a preferred embodiment, these cells are cells derived from the heterohybridoma K6H6B5 (ATCC number CRL-1823) fused to human B cells.

Still another object of the invention is an antibody or a polypeptide comprising Fc region of human IgG, containing from 10% to 55% of fucose, from 60% to 98% of galactose.

This antibody or polypeptide containing from 10% to 55% of fucose, from 60% to 98% of galactose binds to both FcgammaRIIIA, FcgammaRIIA and FcgammaRIIB.

These two properties (the Fc glycosylation profile and the FcgammaR binding profile) are linked together. The applicant shows that these two properties are also related to the fact that this class of antibodies can be produced by a hybridoma cell line.

This antibody or polypeptide can be produced by cells from lymphoid cell lines or lymphoid-derived cell lines or hybridomas or from epithelial kidney cell lines.

Advantageously, this hybridoma cell line is the YB2/0 cell line (ATCC number CRL-1662), derived from the hybridoma cell line, YB2/3HL derived from a myeloma cell line, LOU/C Y3/Ag 1.2.3, fused with spleen cells from an AO rat.

In another embodiment, this antibody or polypeptide is produced from the epithelial kidney cell line VERO (ATCC number CCL-81).

Furthermore, this antibody or polypeptide containing from 10% to 55% of fucose, from 60% to 98% of galactose is obtainable by the step c) i) of the process of preparation described above.

These antibodies or polypeptides belong to the first class described above.

The invention is also directed to a composition comprising at least 80%, preferably at least 95% of this first class of antibodies or polypeptides.

In a preferred embodiment, the composition may comprise at least 80% or 90%, preferably at least 95% or 99% of the antibodies or polypeptides as described above.

It is still a subject of the invention to use this composition to manufacture a medicament for treating cancer such as leukemia, lymphoma, myeloma, Sezary syndrome or solid tumors, auto-immune diseases, allergies, allo-immunization following transplantation, materno-foetal allo-immunization, Graft-Versus Host (GVH) reaction or infectious diseases.

The antibodies of the first class are able to activate a cytotoxic cell (due to their ability to bind FcgammaRIIIA and FcgammaRIIA) in order to kill target cells, for example cancer cells.

Such antibodies will be useful therapeutic tools for triggering the regulation of hematopoietic cell proliferation dependent on Receptor Tyrosine Kinases (RTKs) by FcgammaRIIB. Bifunctional molecules such as anti-RTK IgG antibodies with optimized Fc region capable of efficiently co-aggregating RTKs with FcgammaRIIB could block the proliferation of FcgammaRIIB$^+$ tumor cells.

In a particular aspect of the invention, the materno-foetal allo-immunization treated with this composition is the hemolytic disease of the newborn (HDNB).

This class of antibodies is able to kill red cells, and at the same time to immunomodulate B cells producing antibodies against red cells.

In another particular aspect of the invention, the autoimmune disease is an auto-immune disease involving B cells that produce auto-antibodies such as Systemic Lupus Erythematosis (SLE), Idiopathic Thrombocytopenic Purpura (ITP), Kawasaki syndrome.

In another preferred aspect, the allergies treated are asthma, allergic rhinitis, allergic sinusitis, anaphylactic syndrome, urticaria, angioedema, atopic dermatitis, allergic contact dermatitis and erythema.

Still another object of the invention is an antibody or a polypeptide comprising Fc region of human IgG, characterized in that it contains from 70% to 100% of fucose, for example from 96% to 99%, and from 60% to 98% of galactose, for example from 74% to 89%.

This antibody or polypeptide containing from 70% to 100% fucose and from 60% to 98% galactose binds to both FcgammaRIIA and FcgammaRIIB but does not bind or binds only weakly to FcgammaRIIIA.

The applicant shows that the binding profile is linked to the Fc glycosylation profile. In addition, the applicant shows that this antibodies or polypeptide is produced by cells from a non-lymphoid cell line; thus, the binding profile, the glycosylation profile and the antibody producing cell line are linked.

More particularly, this non-lymphoid cell line is the CHO cell line (ATCC number CCL-61).

In an aspect of particular interest, this antibody or polypeptide is obtainable by the step c) ii) of the process of preparation described above.

These antibodies or polypeptides belong to the second class of antibodies described above.

The invention also embraces a composition comprising at least 80%, preferably at least 95% of antibodies belonging to the second class described above.

In a preferred embodiment, the composition may comprise at least 80%-90%, preferably at least 95% or 99% of the antibodies or polypeptides belonging to the second class described above.

The invention also relates to the use of this composition for the manufacture of a medicament for treating auto-immune diseases, materno-foetal allo-immunization, and inflammatory diseases.

These optimized antibodies that will be useful therapeutic tools for controlling the recruitment of FcgammaRIIB present on mast cells and basophils by allergen-complexed IgG.

As an example, such antibodies with an optimized ability to engage FcgammaRIIB and to trigger FcgammaRIIB inhibitory functions through the subsequent co-aggregation of FcgammaRIIB with FcepsilonRI, once IgE are complexed to the same allergen. Anti-allergen IgG antibodies with an optimized ability to engage FcgammaRIIB and, hence, to trigger FcgammaRIIB inhibitory functions could represent efficient therapeutic tools in the treatment of allergy. As an example, the present invention allows to produce and select anti-FcepsilonRI IgG antibodies with an optimized ability to engage FcgammaRIIB and to trigger FcgammaRIIB inhibitory functions through the subsequent co-aggregation of FcgammaRIIB with FcepsilonRI. Anti-FcepsilonRI IgG antibodies with an optimized ability to engage FcgammaRIIB and, hence, to trigger FcgammaRIIB inhibitory functions could represent efficient therapeutic tools in the treatment of allergy.

The present invention relates to optimized antibodies that will be useful therapeutic tools for controlling the effect of FcgammaRIIB expressed by APC (antigen-presenting cells). Examples of such effects include regulation of antigen presentation and T cell recruitment and regulation of acquired immunity.

In still another aspect, the invention provides an antibody or a polypeptide comprising Fc region of human IgG, this antibody or polypeptide containing from 80% to 100% of fucose, from 60% to 98% of galactose and that contains from 30% to 80% of sialylated forms.

According to the invetion, this antibody or polypeptide does not bind or binds only weakly to FcgammaRIIIA, FcgammaRIIA and FcgammaRIIB.

The applicant shows that the binding profile is linked to the Fc glycosylation profile. The applicant shows also that this class of antibodies (the third class as described above) is produced by cells from a heterohybridoma fused to B cells or EBV-transformed B cells.

In an aspect of particular interest, this antibody or polypeptide is produced by cells from a heterohybridoma fused to B cells.

In a particular embodiment, this heterohybridoma is K6H6B5 (ATCC number CRL-1823) fused to EBV-transformed cells or to B lymphocytes from human donors. This antibody or polypeptide is obtainable by the step c) iii) of the process of preparation described above.

This antibody or polypeptide belong to the third class described above.

The invention is also directed to a composition comprising at least 80%, preferably at least 95% of this antibody or polypeptide belonging to the third class.

In a preferred embodiment, the composition may comprise at least 80%-90%, preferably at least 95% or 99% of the antibodies or polypeptides as described above.

In an aspect of particular interest, this composition is used for the manufacture of a medicament for treating inflammatory diseases, the Crohn disease or Rheumatoid Arthritis.

The antibodies or polypeptides of this third class are unable to trigger inhibitory functions mediated through FcgammaRIIB and to trigger ADCC or another cytotoxic activity. These antibodies or polypeptides are used in the invention to prevent the recruitment of immune effector functions.

Antibodies or polypeptides of particular interest according to the invention belong to the IgG1 subclass.

In another embodiment, antibodies or polypeptides of particular interest belong to the IgG3 subclass.

The invention further relates to the use of a composition as featured above to manufacture a medicament, where the antibody recognizes antigens expressed on or bound to the cell surface of target cells. Said antigens include but are not limited to allo-antigens, transplantation antigens, self-antigens such as class I and class II Major Histocompatibility Antigens (HLA), FcgammaRI, FcgammaRIIA, FcgammaRIII molecules, FcalphaR, FcepsilonRI, B cell receptor, T cell receptor, tumor antigens such as CD20, Her2/NEU, CEA, GD2, allergen such as phospholipase A2, and IgE.

More particularly, the antibodies of the invention recognize Rhesus D antigen to manufacture a medicament for treating or preventing Rhesus allo-immunization of Rh negative patients, leading to the Hæmolytic Disease of the New Born (HDNB).

More particularly, the antibodies of the invention recognize Rhesus D antigen to manufacture a medicament for treating or preventing Idiopathic Thrombocytopenic Purpura (ITP).

More particularly, the antibodies of the invention recognize HLA Class II molecules to manufacture a medicament for treating or preventing cancers, auto-immune diseases, or graft rejections.

Further details are given below in Example 1. Results of these binding and functional tests are presented in the Figures.

FIGURE LEGENDS, RESULTS AND COMMENTS

FIG. 1 represents HPLC profiles of a monoclonal antibody [LFB1 directed against Rhesus D (anti-RhD) antibodies] in order to control the purity and the integrity of the molecule and the absence of polymerized forms: LFB1 monoclonal antibody is composed of 99% of monomers.

FIG. 2 represents the glycosylation patterns of different antibodies directed against Rhesus D (LFB1, LFB2, LFB3), as determined by capillary electrophoresis. The results are expressed as percentage of the different structures identified. The antibodies were produced by different cell lines. LFB1 is produced by YB2/0 cells, LFB2 is produced by CHO cells, and LFB3 is produced by cells from the heterohybridoma K6H6B5 fused to human B cells.

FIG. 3 represents the binding of F(ab)'$_2$ goat anti-human IgG (H+L)-complexed LFB1, LFB2 and LFB3 antibodies to human FcgammaRIIIA expressed on Jurkat-FcgammaRIIIA cells. The binding of LFB1, LFB2 and LFB3 human anti-RhD antibodies to human FcgammaRIIA is assessed by indirect immunofluorescence. Human antibodies (100 ng/ml; 250 ng/ml; 500 ng/ml) are first complexed with F(ab)'$_2$ goat anti-human IgG (H+L) (at doses of 150 ng/ml; 375 ng/ml; 750 ng/ml, respectively) and then incubated with Jurkat-FcgammaRIIIA cells. Binding of LFB1, LFB2 and LFB3 antibodies is then revealed with FITC-labelled-F(ab)'$_2$ mouse anti-human IgG (H+L) (black curves). The dotted curves show background fluorescence of cells incubated with FITC-F(ab)'$_2$ mouse anti-human IgG (H+L) only.

Results and comments: A binding of LFB1 to Jurkat-FcgammaRIIIA cells is always detected from 100 ng/ml to 500 ng/ml. At the highest concentration, almost 50% of Jurkat-FcgammaRIIIA cells are stained. By contrast, no binding of the LFB2 antibody to human FcgammaRIIIA expressed by Jurkat-FcgammaRIIIA cells is observed at 100 ng/ml and only 3% of Jurkat-FcgammaRIIIA cells are weakly labelled at 250 ng/ml and 500 ng/ml. Last, no binding of LFB3 antibody to human FcgammaRIIIA expressed on Jurkat-FcgammaRIIIA cells is observed whatever the concentration tested. Thus, LFB1, produced by YB2/0 cells, with a defined glycosylation pattern, is an example of a monoclonal antibody which binds to FcgammaRIIIA. Moreover, LFB2, produced by CHO cells, and LFB3, produced by cells from the heterohybridoma K6H6B5 fused to B cells, with different but defined glycosylation patterns, are examples of monoclonal antibodies which do not bind or bind only weakly to FcgammaRIIIA.

Figure 4:
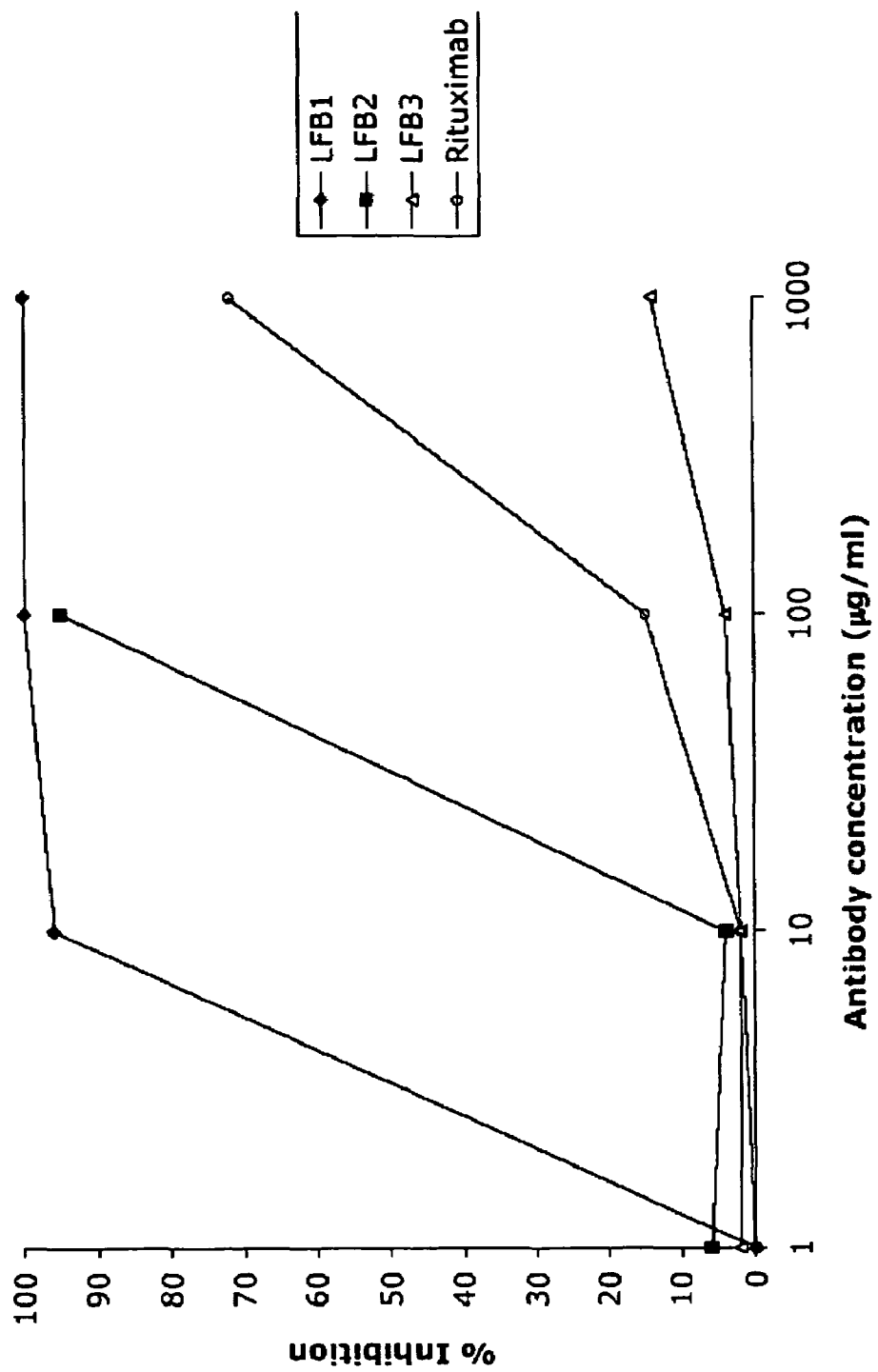

FIG. 4 represents the inhibition of 3G8-PE binding to human FcgammaRIIIA expressed on Jurkat-FcgammaRIIIA cells by monomeric LFB1, LFB2, LFB3, or Rituximab antibodies. Jurkat-FcgammaRIIIA cells are first incubated with various concentrations of monomeric LFB1 (from 1 microg/ml to 1000 microg/ml), or monomeric LFB2 (from 1 microg/ml to 100 microg/ml), or monomeric LFB3 (from 1 microg/ml to 1000 microg/ml), or monomeric Rituximab (from 1 microg/ml to 1000 microg/ml), and then with 0.01 microg/ml of 3G8-PE. The binding of PE-labelled mouse 3G8 monoclonal antibody to human FcgammaRIIIA in presence or absence of monomeric antibodies as competitors is then assessed by direct immunofluorescence.

Results and comments: Monomeric LFB1 induces a dose-dependent inhibition of 3G8-PE binding to human FcgammaRIIIA expressed on Jurkat-FcgammaRIIIA cells. 10 microg/ml of LFB1 induces a decrease of 96% of the percentage of labelled cells with 3G8-PE, whereas only a 2% decrease is achieved with 10 microg/ml of Rituximab. At the highest dose used (1000 microg/ml), LFB1 induces a 100% inhibition (72% with 1000 microg/ml of Rituximab). Monomeric LFB2 induces an inhibition of 3G8-PE binding to FcgammaRIIIA lower than that obtained with LFB1. 10 microg/ml of LFB2 induces a decrease of the percentage of labelled cells with 3G8-PE lower than 5%. However, at a high concentration (100 microg/ml), a decrease of about 95% of the percentage of stained Jurkat-FcgammaRIIIA cells is observed (as compared to only 15% with the same dose of Rituximab). By contrast, the inhibition induced by monomeric LFB3 is very weak whatever the doses used. The inhibition is lower than 20% when 1000 microg/ml of LFB3 are used.

Thus, this assay shows that antibodies under monomeric forms exhibit different binding capacities to FcgammaRIIIA depending on the cell lines that produce them and on their glycosylation profiles.

Figure 5:
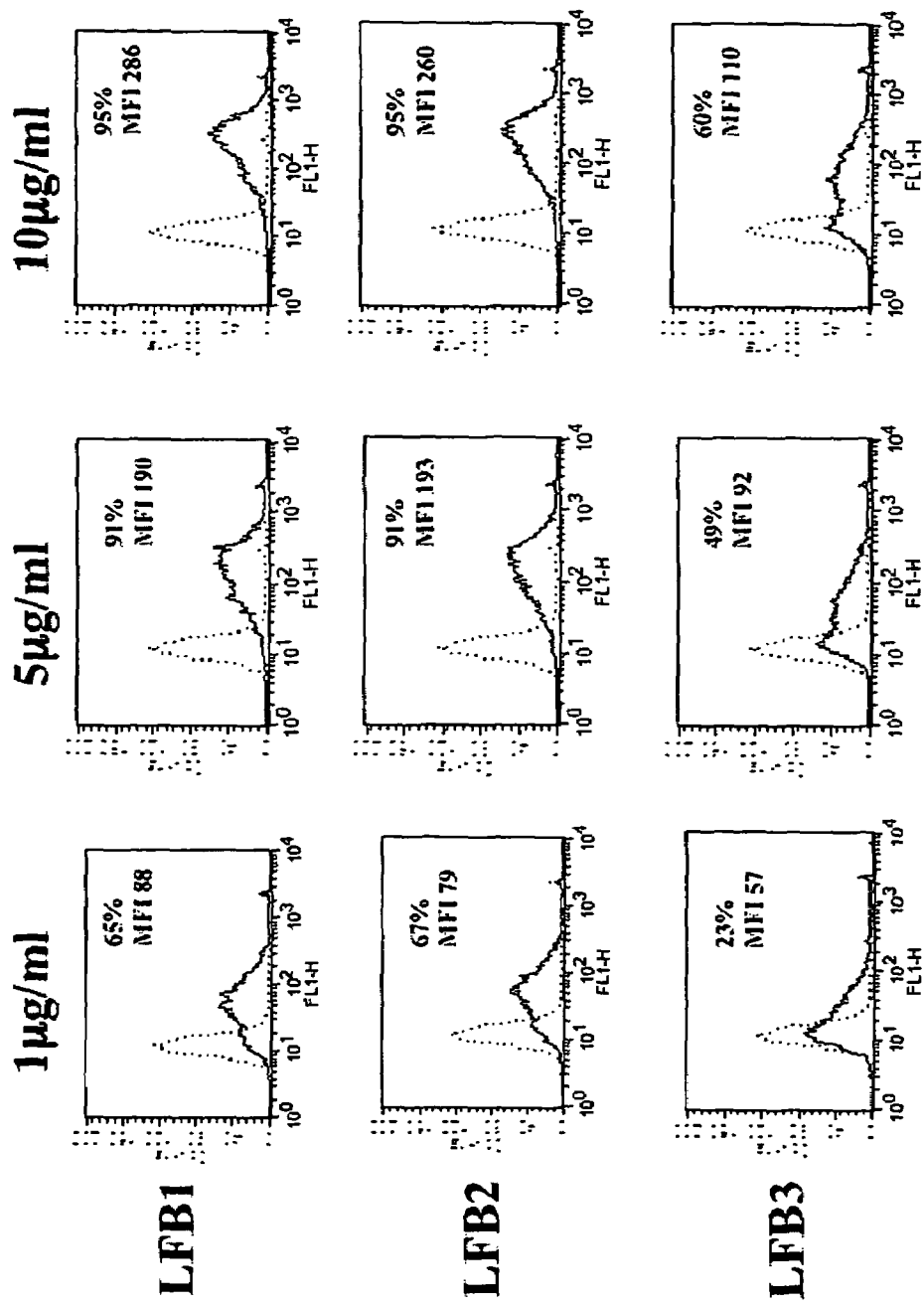

FIG. 5 represents the binding of F(ab)'$_2$ goat anti-human IgG (H+L)-complexed LFB1, LFB2 and LFB3 antibodies to human FcgammaRIIA expressed on K562 cells. The binding of LFB1, LFB2 and LFB3 human anti-RhD antibodies to human FcgammaRIIA is assessed by indirect immunofluorescence. Human antibodies (1 µg/ml; 5 µg/ml; 10 µg/ml) are first complexed with F(ab)'$_2$ goat anti-human IgG (H+L) (at doses of 1.5 µg/ml; 7.5 µg/ml; 15 µg/ml, respectively) and then incubated with K562 cells. Binding of LFB1, LFB2 and LFB3 antibodies is then revealed with FITC labelled-F(ab)'$_2$ mouse anti-human IgG (H+L) (black curves). The dotted curves show background fluorescence of cells incubated with FITC-F(ab)'$_2$ mouse anti-human IgG (H+L) only.

Results and comments: LFB1 antibody binds to K562 cells even at a low dose such as 1 µg/ml (more than 50% of K562 cells are stained at this low concentration). At the highest dose of LFB1 antibody (10 µg/ml), almost 100% of K562 cells are labelled. LFB2 has the same binding pattern to human FcgammaRIIA expressed on K562 cells as LFB1. LFB2 binds to human FcgammaRIIA whatever the dose used (from 1 µg/ml to 10 µg/ml), with almost 100% of K562 cells stained with 10 µg/ml. By contrast, K562 cells are weakly labelled with 1 µg/ml, 5 µg/ml or 10 µg/ml of LFB3. Thus, LFB1, produced by YB2/0 cells, and LFB2, produced by CHO cells, with different but defined glycosylation patterns, are examples of monoclonal antibodies which bind to FcgammaRIIA. Moreover, LFB3, produced by cells from the heterohybridoma K6H6B5 fused to B cells, with a defined glycosylation pattern, is an example of monoclonal antibodies which do not bind or bind only weakly to FcgammaRIIA.

Figure 6:
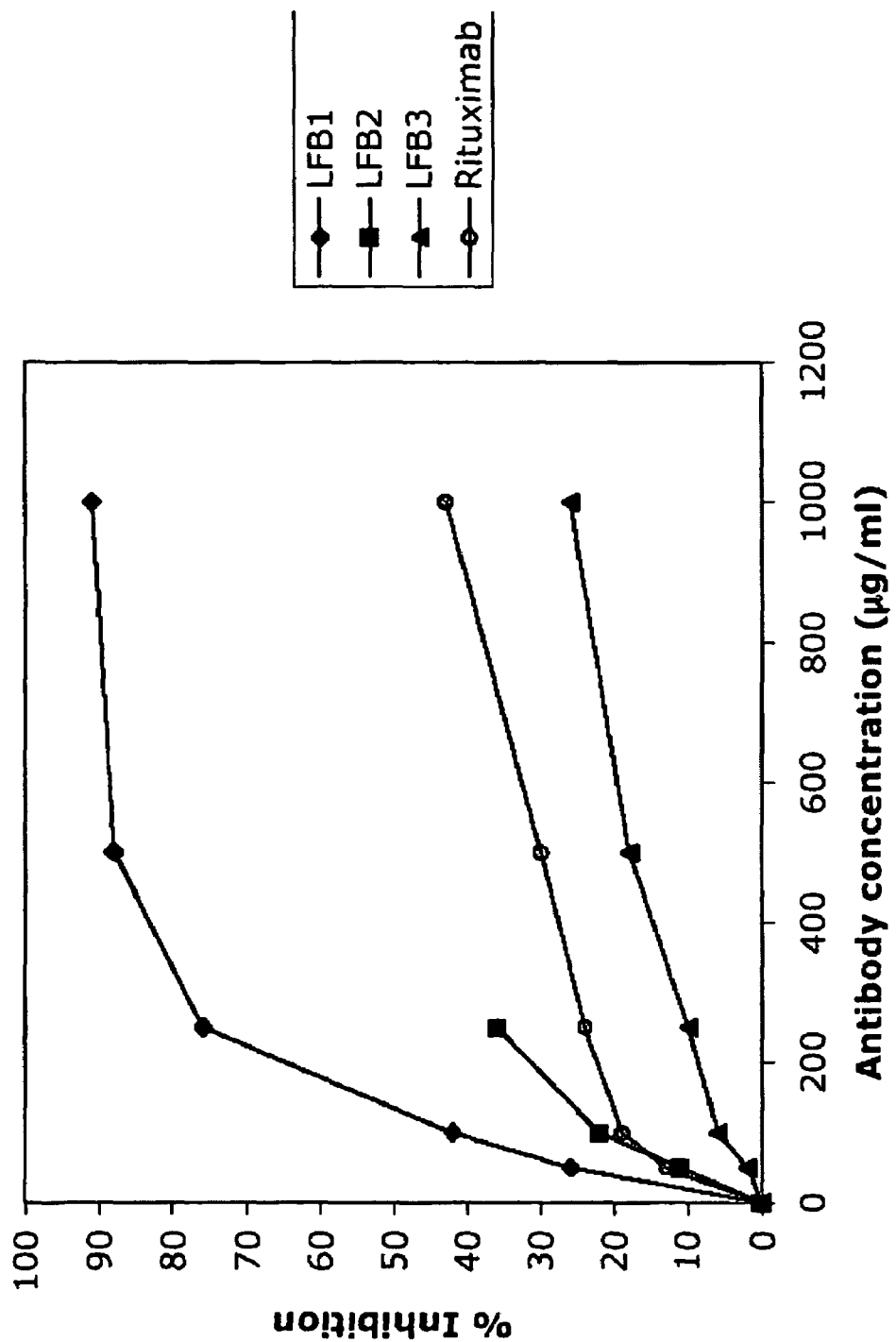

FIG. 6 represents the inhibition of AT10-FITC (directed against FcgammaRIIA and FcgammaRIIB) binding to human FcgammaRIIA expressed on K562 cells by monomeric LFB1, LFB2, LFB3, or Rituximab antibodies. K562 cells are first incubated with various concentrations of monomeric LFB1 (from 50 µg/ml to 1000 µg/ml), or monomeric LFB2 (from 50 µg/ml to 250 µg/ml), or monomeric LFB3 (from 50 µg/ml to 1000 µg/ml), or monomeric Rituximab (from 50 µg/ml to 1000 µg/ml), and then with 0.25 µg/ml of AT10-FITC. The binding of FITC-labelled mouse AT10 monoclonal antibody to human FcgammaRIIA in presence or absence of monomeric antibodies as competitors is assessed by direct immunofluorescence.

Results and comments: monomeric LFB1 induces a dose-dependent inhibition of AT10-FITC binding to human FcgammaRIIA expressed on K562 cells. 100 µg/ml of LFB1 induces a decrease of almost 50% of the percentage of labelled cells with AT10-FITC, whereas only a 19% decrease is achieved with 100 µg/ml of Rituximab. At the highest dose used (1000 µg/ml), the decrease is up to 90% (as compared to 43% with 1000 µg/ml of Rituximab). Monomeric LFB2 induces also a dose-dependent inhibition of AT10-FITC binding to FcgammaRIIA. A decrease of about 40% of the percentage of stained K562 cells is observed for the highest concentration of LFB2 used (250 µg/ml) (as compared to 24% with the same dose of Rituximab). By contrast, the inhibition induced by monomeric LFB3 is weak. The inhibition is lower than 30% when 1000 µg/ml of LFB3 are used. Thus, this assay shows that antibodies under monomeric forms exhibit different binding capacities to FcgammaRIIA depending on the cell lines that produce them and on their glycosylation profiles.

Figure 7:
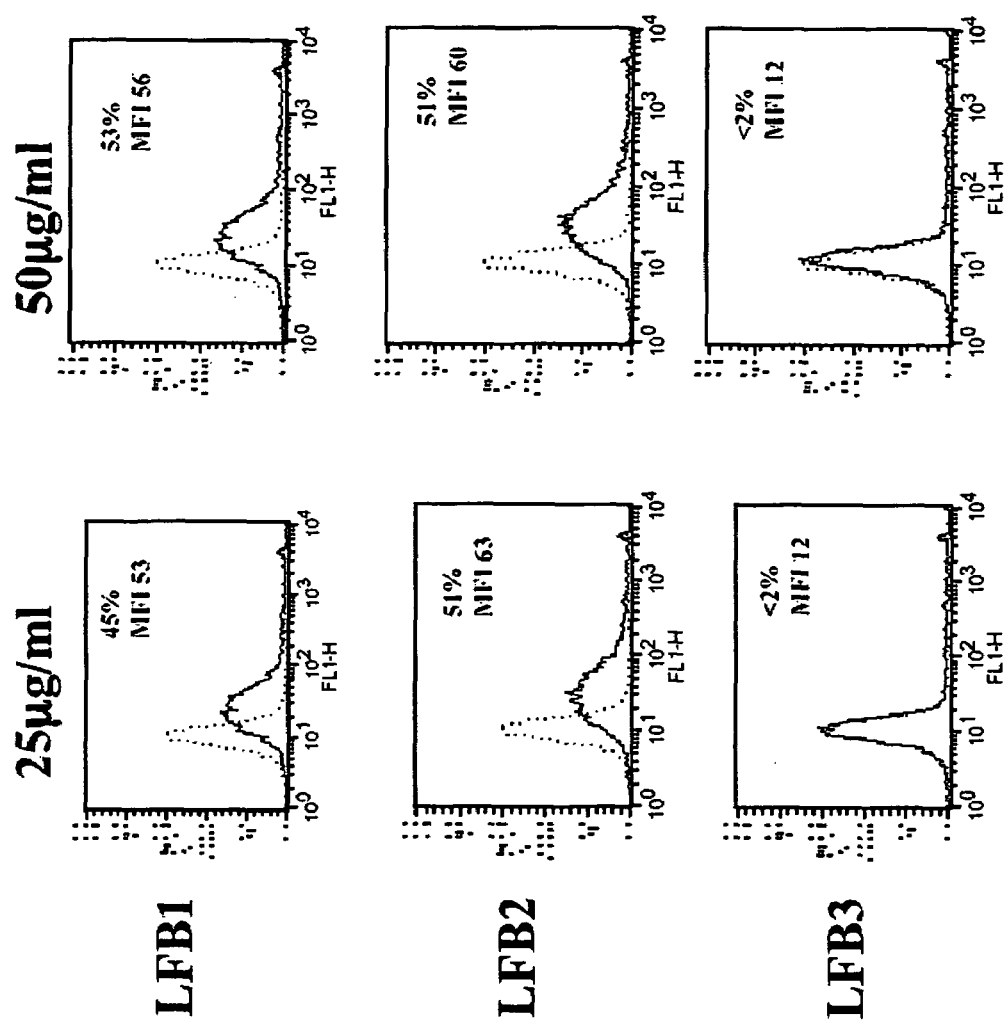

FIG. 7 represents the binding of F(ab)'$_2$ goat anti-human IgG (H+L)-complexed LFB1, LFB2 and LFB3 antibodies to human FcgammaRIIB expressed on IIA1.6-huFcgammaRIIB cells. The binding of LFB1, LFB2 and LFB3 human anti-RhD antibodies to human FcgammaRIIB is assessed by indirect immunofluorescence. Human antibodies (25 µg/ml; 50 µg/ml) are first complexed with F(ab)'$_2$ goat anti-human IgG (H+L) (at doses of 37.5 µg/ml; 75 µg/ml, respectively) and then incubated with ILA1.6-huFcgammaRIIB cells. Binding of LFB1, LFB2 and LFB3 antibodies is then revealed with FITC labelled-F(ab)'$_2$ mouse anti-human IgG (H+L) (black curves). The dotted curves show background fluorescence of cells incubated with FITC-F(ab)'$_2$ mouse anti-human IgG (H+L) only.

Results and comments: LFB1 antibody binds to IIA1.6-huFcgammaRIIB cells at 25 µg/ml and 50 µg/ml (more than 50% of IIA1.6-huFcgammaRIIB cells are stained at 50 µg/ml). LFB2 antibody has the same binding pattern to human FcgammaRIIB as LFB1. LFB2 binds to human FcgammaRIIB whatever the dose used with more than 50% of IIA1.6-huFcgammaRIIB cells labelled at 50 µg/ml. By contrast, no binding of LFB3 antibody to human FcgammaRIIB is observed whatever the concentration tested. Thus, LFB1, produced by YB2/0 cells, and LFB2, produced by CHO cells, with different but defined glycosylation patterns, are examples of monoclonal antibodies which bind to FcgammaRIIB. Moreover, LFB3, produced by cells from the heterohybridoma K6H6B5 fused to B cells, with a defined glycosylation pattern, is an example of monoclonal antibodies which do not bind or bind only weakly to FcgammaRIIB.

Figure 8:
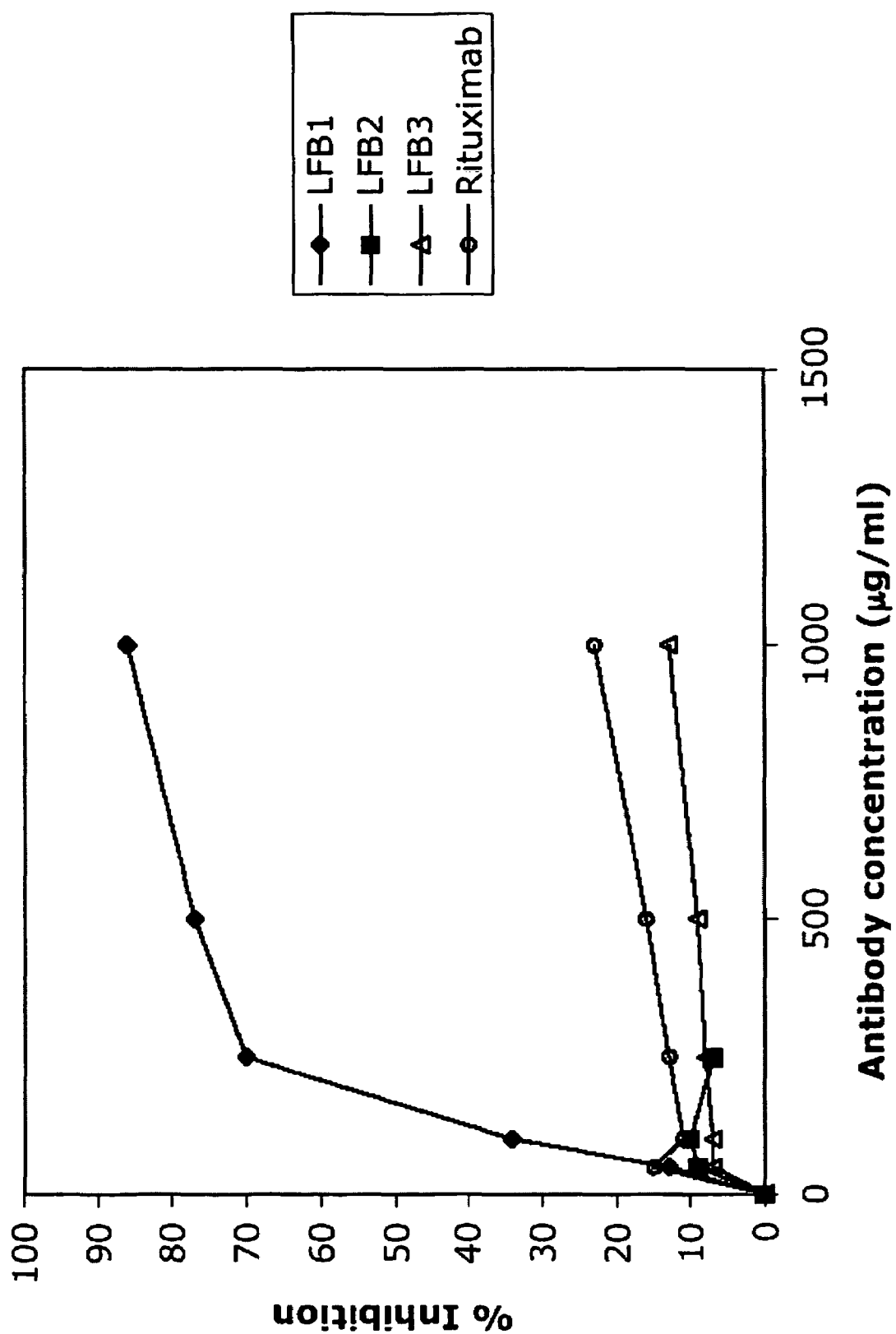

FIG. 8 represents the inhibition of AT10-FITC binding to human FcgammaRIIB expressed on IIA1.6-huFcgammaRIIB cells by monomeric LFB1, LFB2, LFB3, and Rituximab antibodies. IIA1.6-huFcgammaRIIB cells are first incubated with various concentrations of monomeric LFB1 (from 50 µg/ml to 1000 µg/ml), or monomeric LFB2 (from 50 µg/ml to 250 µg/ml), or monomeric LFB3 (from 50 µg/ml to 1000 µg/ml), or monomeric Rituximab (from 50 µg/ml to 1000 µg/ml), and then with 0.25 µg/ml of AT10-FITC. The binding of FITC-labelled mouse AT10 monoclonal antibody to human FcgammaRIIB in presence or absence of monomeric antibodies as competitors is then assessed by direct immunofluorescence.

Results and comments: monomeric LFB1 induces a dose-dependent inhibition of AT10-FITC binding to human FcgammaRIIB expressed on IIA1.6-huFcgammaRIIB cells. 100 µg/ml of LFB1 induces a decrease of almost 40% of the percentage of labelled cells with AT10-FITC, whereas only an 11% decrease is achieved with 100 µg/ml of Rituximab. At the highest dose used (1000 µg/ml), the decrease is up to 80% (as compared to 23% with 1000 µg/ml of Rituximab). Monomeric LFB2 induces a lower inhibition of AT10-FITC binding to FcgammaRIIB than the inhibition obtained with LFB1, although similar to the inhibition provoked by monomeric Rituximab (a decrease of about 10% of labelled cells with AT10-FITC is observed when 100 µg/ml of these antibodies are used). The inhibition induced by monomeric LFB3 is weak, since the decrease of the percentage of labelled cells with AT10-FITC is lower than 20% when 1000 µg/ml of LFB3 are used.

Thus, this assay shows that antibodies under monomeric forms exhibit different binding capacities to FcgammaRIIB depending on the cell lines that produce them and on their glycosylation profiles.

FIG. 9 summarizes the glycosylation profile and the ID10, ID30, ID50 of LFB1, LFB2, LFB3 and of Rituximab, evaluated by competition assays. LFB1, which exhibits an ID50 of 0.02 microM when FcgammaRIIIA is tested, an ID50 of 0.85 microM when FcgammaRIIA is tested, and an ID50 of 1 microM when FcgammaRIIB is tested, is an example of monoclonal antibodies which "bind to" FcgammaRIIIA, FcgammaRIIA, and FcgammaRIIB.

LFB3, which exhibits an ID50>6 microM when FcgammaRIIIA is tested, an IDS0>6 microM when FcgammaRIIA is tested, and an ID50>6 microM when FcgammaRIIB is tested, is an example of monoclonal antibodies which "do not bind or bind only weakly" to FcgammaRIIIA, FcgammaRIIA, and FcgammaRIIB.

Figure 10:
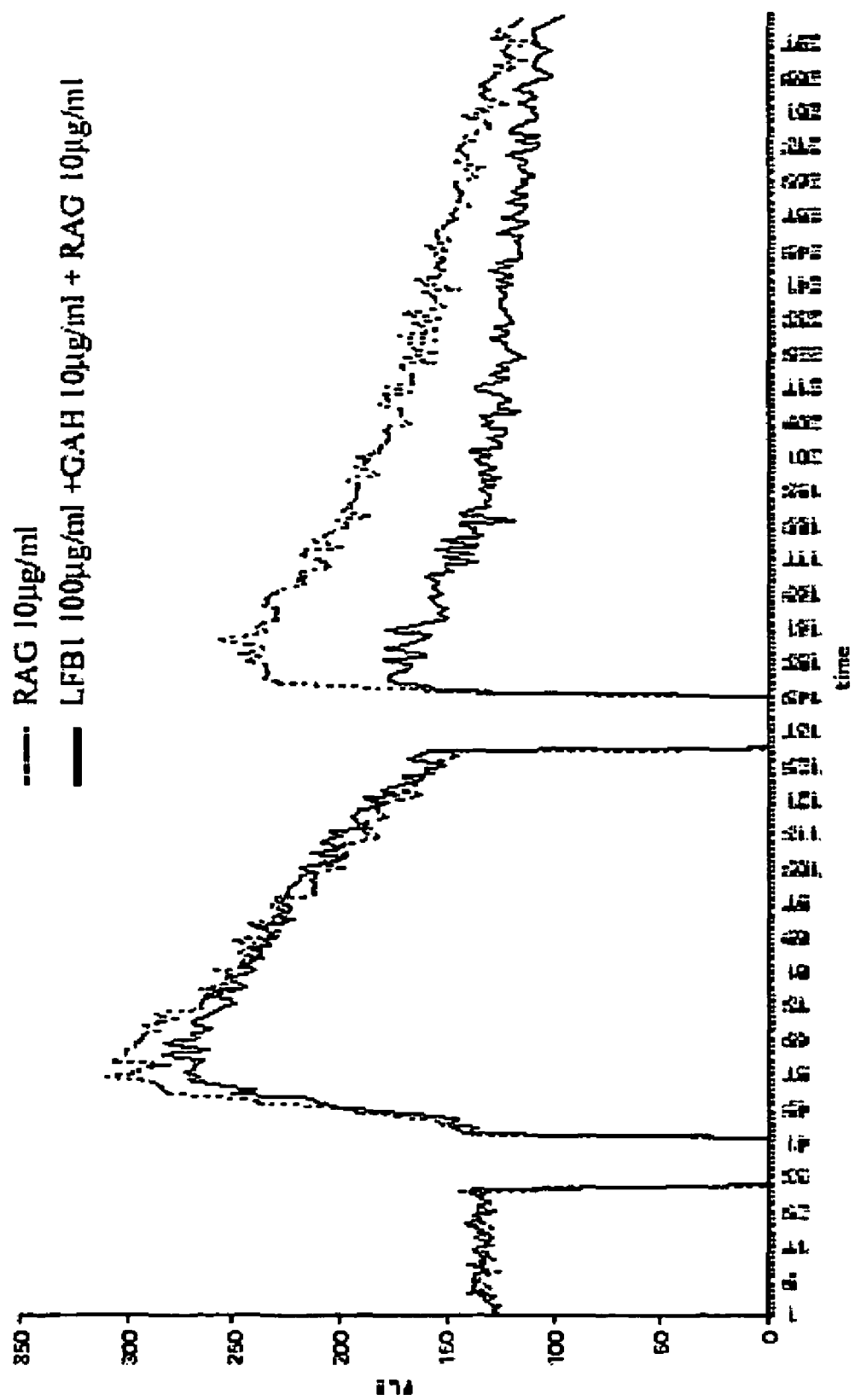

FIG. 10 represents the inhibition of calcium mobilization by LFB1 human anti-RhD antibody. IIA1.6-huFcgammaRIIB cells are stimulated either with F(ab)'$_2$ rabbit anti-goat IgG (RAG) (10 µg/ml) that cross-react with mouse Ig or with LFB1 antibody (100 µg/ml) in presence of F(ab)'$_2$ goat anti-human IgG (H+L) (GAH) (10 µg/ml) and F(ab)'$_2$ rabbit anti-goat IgG (RAG) (10 µg/ml). This latter assay allows to efficiently cross-link murine surface IgG with the human FcgammaRIIB expressed by IIA1.6-huFcgammaRIIB cells via the human monoclonal IgG antibody bound to this receptor. The BCR-mediated $Ca^{2+}$ influx induced with F(ab)'$_2$ RAG (10 µg/ml) is compared to the $Ca^{2+}$ influx observed following BCR/FcgammaRIIB cross-linking. Intracellular free $Ca^{2+}$ levels in Fluo-3 AM loaded cells are monitored by flow cytometry. $Ca^{2+}$ release from intracellular $Ca^{2+}$ stores is measured in presence of 1 mM EGTA (left part of the curves), and $Ca^{2+}$ entering the cells is measured after addition of 6 mM $CaCl_2$ (right part of the curves).

Results and comments: the addition of F(ab)'$_2$ rabbit anti-goat IgG (RAG) antibodies triggers calcium release from the intracellular stores (left peak of the curve, dotted line) as well as a calcium influx into IIA1.6-huFcgammaRIIB cells (right peak of the curve, dotted line). A strong inhibition of the calcium influx (right peak of the curve, black line), a characteristics of the engagement of FcgammaRIIB on B cells, is obtained by incubating IIA1.6-huFcgammaRIIB cells with LFB1 antibody (100 µg/ml) in presence of F(ab)'$_2$ goat anti-human IgG (H+L) (GAH) (10 µg/ml) and F(ab)'$_2$ rabbit anti-goat IgG (RAG) (10 µg/ml). As expected when the FcgammaRIIB inhibitory function is triggered, no inhibition of the calcium release from intracellular stores is observed (left peak of the curve, black line). Thus, this experiment shows that the LFB1 monoclonal antibody is capable of triggering inhibitory functions mediated through FcgammaRIIB expressed on lymphoma B cells, a triggering which leads to the blockade of B cell activation and differentiation into antibody-producing cells.

Figure 11:
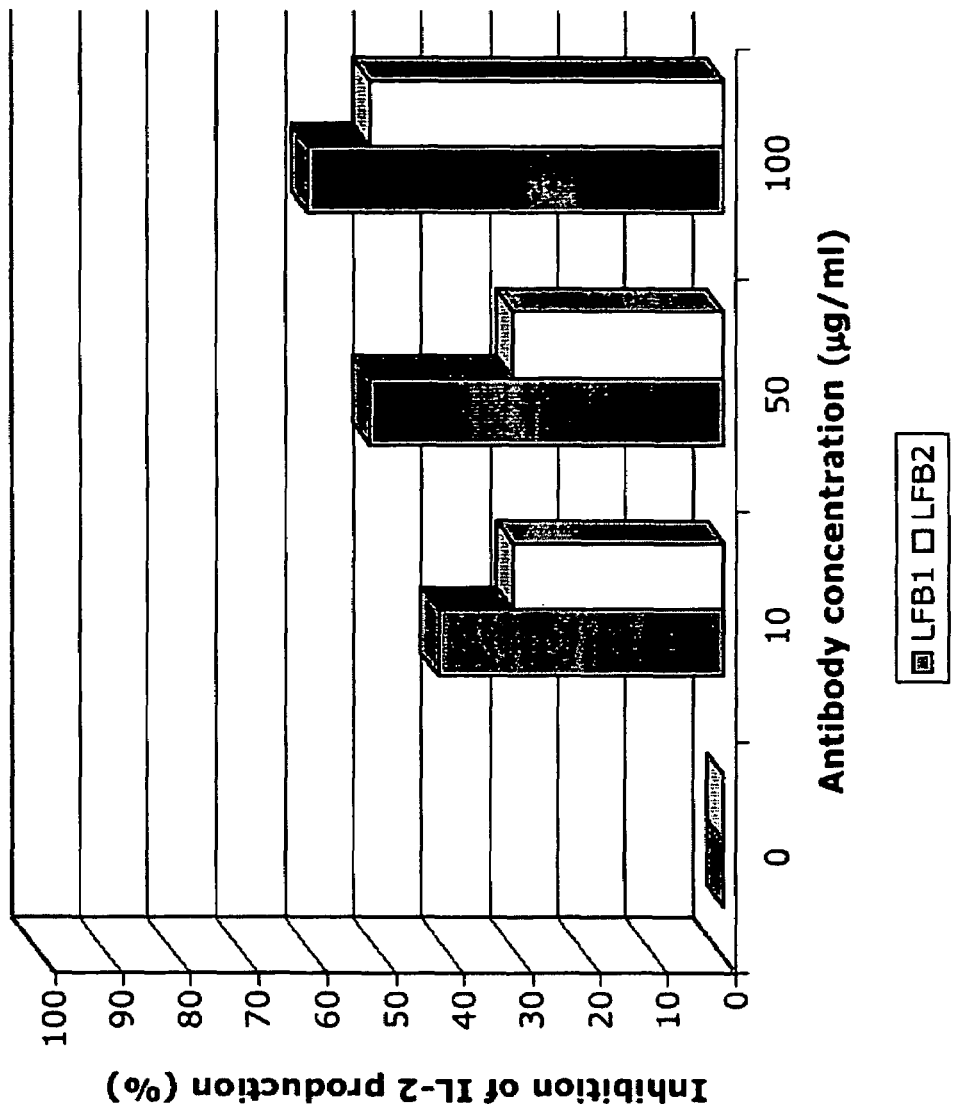

FIG. 11 represents the inhibition of IL-2 production by LFB1 and LFB2 human anti-RhD antibodies. $5 \times 10^5$ IIA1.6-huFcgammaRIIB cells are stimulated for 22 h either with 50 µg/ml F(ab)'$_2$ rabbit anti-goat IgG (RAG) alone or with 50 µg/ml F(ab')$_2$ rabbit anti-goat IgG and LFB1 or LFB2 antibody at different concentrations as indicated in abscissa (from 10 to 100 µg/ml). The RAG F(ab)'$_2$ fragments cross-react with both murine and human IgG, allowing to cross-link the mouse surface IgG expressed by IIA1.6 huFcgammaRIIB positive cells and the human monoclonal IgG antibody bound to FcgammaRIIB. The secretion of mouse IL-2 by IIA1.6-huFcgammaRIIB cells in cell culture supernatants is measured by an ELISA assay using 1 µg/ml rat anti-mouse IL-2 as capture antibody and 1 µg/ml biotinylated rat anti-mouse IL-2 as detection antibody. Results and comments: the stimulation of IIA1.6-huFcgammaRIIB positive cells that express surface IgG by F(ab)'$_2$ rabbit anti-goat IgG (RAG) cross-reacting with mouse IgG triggers the secretion of IL-2 (about 380 pg/ml after 22 h of culture of $5 \times 10$ IIA1.6 FcgammaRIIB cells). The presence of various doses of LFB1 antibody (from 10 µg/ml to 100 µg/ml), in presence of RAG F(ab)'$_2$ fragments cross-reacting with both murine and human IgG, induces a dose-dependent inhibition of IL-2 secretion. As low as 10 µg/ml of LFB1 antibody induces about a 40% inhibition of IL-2 production. At the highest dose used of LFB1 (100 µg/ml), the inhibition of IL-2 production reaches 60%. Moreover, LFB2 antibody also inhibits IL-2 production by ILA1.6-huFcgammaRIIB1 cells cultured in presence of RAG F(ab)'$_2$. LFB2 induces a dose-dependent inhibition of IL-2 production since the presence of 10 µg/ml of this antibody induces a 30% inhibition of IL-2 secretion, while 100 µg/ml of LFB2 induces about 50% inhibition of IL-2 production.

Thus, this experiment shows that LFB1, produced by YB2/0 cells, and LFB2, produced by CHO cells, which bind to FcgammaRIIB expressed by IIA1.6-huFcgammaRIIB cells, are examples of monoclonal antibodies capable of triggering inhibitory functions mediated through FcgammaRIIB expressed on B cells. Notably, these antibodies lead to the blockade of cytokine production by these cells.

Figure 12:
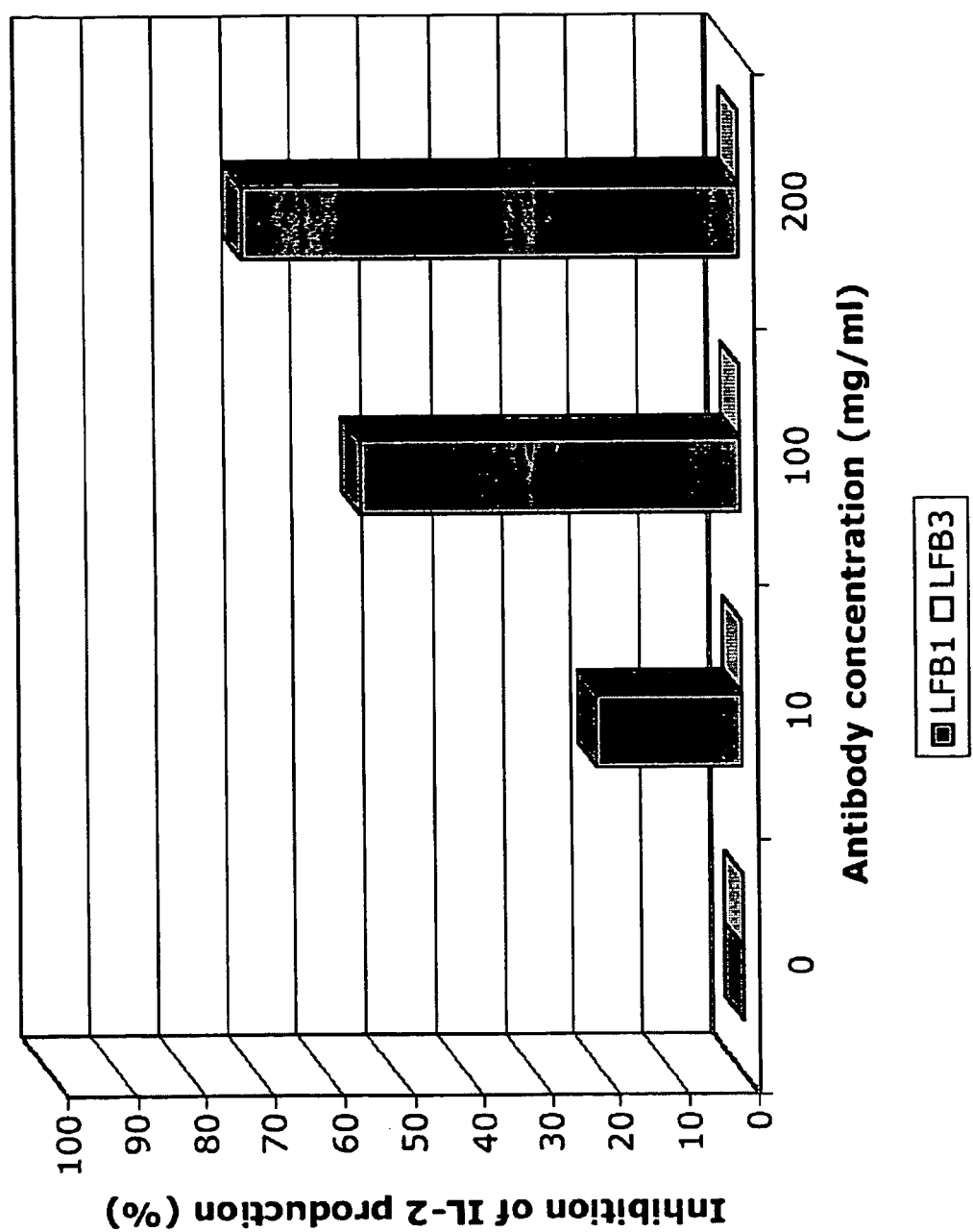

FIG. 12 represents the inhibition of IL-2 production by LFB1 but not by LFB3 human anti-RhD antibodies. $5 \times 10^5$ IIA1.6-huFcgammaRIIB cells are stimulated for 22 h either with 50 µg/ml F(ab)'$_2$ rabbit anti-goat IgG (RAG) alone or with 50 µg/ml F(ab')$_2$ rabbit anti-goat IgG and LFB1 or LFB3 antibody at different concentrations as indicated in abscissa (from 10 μg/ml to 200 μg/ml). The RAG F(ab)'$_2$ fragments cross-react with both murine and human IgG, allowing to cross-link the mouse surface IgG expressed by ILA1.6 huFcgammaRIIB positive cells and the human monoclonal IgG antibody bound to FcgammaRIIB. The production of mouse IL-2 by ILA1.6-huFcgammaRIIB cells in cell culture supernatants is measured by an ELISA assay using 1 μg/ml rat anti-mouse IL-2 as capture antibody and 1 μg/ml biotinylated rat anti-mouse IL-2 as detection antibody.

Results and comments: LFB1 antibody (from 10 μg/ml to 200 μg/ml) induces a dose-dependent inhibition of IL-2 secretion. As low as 10 μg/ml of LFB1 antibody induces about a 20% inhibition of IL-2 production, while 100 μg/ml induces up to 50% inhibition. At the highest dose used of LFB1 (200 μg/ml), the inhibition of IL-2 production reaches 70%. By contrast, LFB3 antibody does not inhibit IL-2 production by IIA1.6-huFcgammaRIIB cells cultured in presence of RAG F(ab)'$_2$ fragments, even when used at a high dose such as 200 μg/ml (<3% decrease). Thus, this experiment shows that the LFB1 monoclonal antibody, produced by YB2/0 cells which binds to FcgammaRIIB expressed by IIA1.6-huFcgammaRIIB1 cells, is an example of monoclonal antibody capable of triggering inhibitory functions mediated through FcgammaRIIB expressed on B cells. Notably, it leads to the blockade of IL-2 production by B cells. In addition, this experiment also shows that the LFB3 monoclonal antibody, produced by cells from the heterohybridoma K6H6B5 fused to B cells, which does not bind to FcgammaRIIB expressed by IIA1.6-huFcgammaRIIB1 cells, is an exemple of monoclonal antibody unable to trigger inhibitory functions mediated through FcgammaIIB expressed on B cells.

EXAMPLE 1

Selection of Anti-RhD Antibodies with Improved Properties to Trigger FcgammaRIIB Mediated Inhibition Material and Methods The method of the present invention for selecting an immunologically active molecule is described below using human IgG antibodies directed against RhD antigen. As examples, LFB1, LFB2, and LFB3 human monoclonal antibodies directed against Rhesus D are being used.

The capacity of the purified human antibodies, either complexed with F(ab)'$_2$ anti-human Ig or not, to bind FcgammaRIIB1 expressed on indicator cells (mouse IIA1.6 lymphoma B cells expressing a functional mouse BCR and a human recombinant FcgammaRIIB1, termed IIA1.6-huFcgammaRIIB1) is measured by a fluorescence antibody assay (complexed) or by a immunofluorescence competition assay (monomeric), respectively.

The capacity of the purified human antibody to induce the inhibition of calcium mobilization can be assessed by a calcium measurement assay. Inhibition of calcium mobilization is evaluated by co-aggregating the purified human antibody bound to FcgammaRIIB with BCR expressed on indicator cells (mouse IIA1.6 lymphoma B cells expressing a functional mouse BCR and a human recombinant FcgammaRIIB1). It is compared to BCR-mediated calcium mobilization induced with F(ab)'$_2$ rabbit anti-goat IgG (RAG) that cross react with mouse IgG.

The capacity of the purified human antibody to induce the inhibition of interleukin-2 (IL-2) production can be measured by an enzyme-linked immunosorbent assay (ELISA) that detects and quantifies IL-2. Inhibition of IL-2 production is evaluated by co-aggregating the purified human or chimeric antibody bound to FcgammaRIIB with BCR expressed on indicator cells (mouse IIA1.6 lymphoma B cells expressing a functional mouse BCR and a human recombinant FcgammaRIIB1). It is compared to BCR-mediated IL-2 production induced with F(ab)'$_2$ goat anti-mouse IgG (H+L).

Cell Lines and Antibodies

The mouse IIA1.6 B cell lymphoma is a FcgammaR-defective variant of A20 B cells (Jones et al., 1986) that bears a deletion of the 5' end of the FcgammaRII gene (Lewis et al., 1986; Bonnerot et al., 1991) and does not transcribe the genes encoding the alpha- and the gamma-chains of mouse FcgammaRIII (Bonnerot et al.,1991). IIA.1.6 cells were transfected by the cDNA encoding FcgammaRIIB1 obtained from Dr. M. Hogarth (Melbourne University, Parkville, Victoria, Australia) (Hogarth et al., 1987). IIA1.6 and IIA1.6-huFcgammaRIIB1 cells were cultured in Click medium [RPMI 1640 (GIBCO, Paisley, Scotland) supplemented with 10% heat-inactivated FCS (Hyclone Laboratories Inc., Logan, Utah, USA), 100 U/ml penicillin, 100 μg/ml streptomycin, 2 mM L-glutamine, 5 mM sodium pyruvate, 0.5 μM 2-β-mercaptoethanol.

The YB2/0 cell line (ATCC number CRL-1662) was used to produce a human recombinant anti-Rh D (LFB1) monoclonal antibody. YB2/0 transfected cells were cultured in a specific EM culture medium with 5% of FCS.

CHO dhfr- (Columbia University, New York, USA) cells were cultured in a specific EM culture medium supplemented with 5% of FCS to produce the LFB2 anti Rh D human recombinant antibody.

The sequence of the constant region of the heavy chain of LFB1/LFB2 antibody (starting at the 5' end of the CH1 as defined by Kabat) is shown below (SEQ ID No 5):

```
  1 GCCTCCACCA AGGGCCCATC GGTCTTCCCC CTGGCACCCT CCTCCAAGAG

51 CACCTCTGGG GGCACAGCGG CCCTGGGCTG CCTGGTCAAG GACTACTTCC

101 CCGAACCGGT GACGGTGTCG TGGAACTCAG GCGCCCTGAC CAGCGGCGTG

151 CACACCTTCC CGGCTGTCCT ACAGTCCTCA GGACTCTACT CCCTCAGCAG

201 CGTGGTGACC GTGCCCTCCA GCAGCTTGGG CACCCAGACC TACATCTGCA

251 ACGTGAATCA CAAGCCCAGC AACACCAAGG TGGACAAGAA AGTTGAGCCC

301 AAATCTTGTG ACAAAACTCA CACATGCCCA CCGTGCCCAG CACCTGAACT

351 CCTGGGGGGA CCGTCAGTCT TCCTCTTCCC CCCAAAACCC AAGGACACCC
```

```
-continued
401 TCATGATCTC CCGGACCCCT GAGGTCACAT GCGTGGTGGT GGACGTGAGC

451 CACGAAGACC CTGAGGTCAA GTTCAACTGG TACGTGGACG GCGTGGAGGT

501 GCATAATGCC AAGACAAAGC CGCGGGAGGA GCAGTACAAC AGCACGTACC

551 GTGTGGTCAG CGTCCTCACC GTCCTGCACC AGGACTGGCT GAATGGCAAG

601 GAGTACAAGT GCAAGGTCTC CAACAAAGCC CTCCCAGCCC CCATCGAGAA

651 AACCATCTCC AAAGCCAAAG GGCAGCCCCG AGAACCACAG GTGTACACCC

701 TGCCCCCATC CCGGGATGAG CTGACCAAGA ACCAGGTCAG CCTGACCTGC

751 CTGGTCAAAG GCTTCTATCC CAGCGACATC GCCGTGGAGT GGGAGAGCAA

801 TGGGCAGCCG GAGAACAACT ACAAGACCAC GCCTCCCGTG CTGGACTCCG

851 ACGGCTCCTT CTTCCTCTAC AGCAAGCTCA CCGTGGACAA GAGCAGGTGG

901 CAGCAGGGGA ACGTCTTCTC ATGCTCCGTG ATGCATGAGG CTCTGCACAA

951 CCACTACACG CAGAAGAGCC TCTCCCTGTC TCCGGGTAAA
```

The B cell line which produces the anti-Rh D LFB3 antibody was obtained by fusing human B lymphocytes from a donor immunized with human Rh positive red blood cells with the heteromyeloma cell line K6H6/B5 (ATCC number CRL-1823) and subsequent cloning was performed by limiting dilutions. LFB3 cells were cultured in RPMI 1640 medium supplemented with 5% FCS.

The sequence of the constant region of the heavy chain of LFB3 antibody (starting at the 5' end of the CH1 as defined by Kabat) is shown below (SEQ ID No 6):

```
  1 GCCTCCACCA AGGGCCCATC GGTCTTCCCC CTGGCACCCT CCTCCAAGAG

51 CACCTCTGGG GGCACAGCGG CCCTGGGCTG CCTGGTCAAG GACTACTTCC

101 CCGAACCGGT GACGGTGTCG TGGAACTCAG GCGCCCTGAC CAGCGGCGTG

151 CACACCTTCC CGGCTGTCCT ACAGTCCTCA GGACTCTACT CCCTCAGCAG

201 CGTGGTGACC GTGCCCTCCA GCAGCTTGGG CACCCAGACC TACATCTGCA

251 ACGTGAATCA CAAGCCCAGC AACACCAAGG TGGACAAGAG AGTTGAGCCC

301 AAATCTTGTG ACAAAACTCA CACATGCCCA CCGTGCCCAG CACCTGAACT

351 CCTGGGGGGA CCGTCAGTCT TCCTCTTCCC CCCAAAACCC AAGGACACCC

401 TCATGATCTC CCGGACCCCT GAGGTCACAT GCGTGGTGGT GGACGTGAGC

451 CACGAAGACC CTGAGGTCAA GTTCAACTGG TACGTGGACG GCGTGGAGGT

501 GCATAATGCC AAGACAAAGC CGCGGGAGGA GCAGTACAAC AGCACGTACC

551 GTGTGGTCAG CGTCCTCACC GTCCTGCACC AGGACTGGCT GAATGGCAAG

601 GAGTACAAGT GCAAGGTCTC CAACAAAGCC CTCCCAGCCC CCATCGAGAA

651 AACCATCTCC AAAGCCAAAG GGCAGCCCCG AGAACCACAG GTGTACACCC

701 TGCCCCCATC CCGGGAGGAG ATGACCAAGA ACCAGGTCAG CCTGACCTGC

751 CTGGTCAAAG GCTTCTATCC CAGCGACATC GCCGTGGAGT GGGAGAGCAA

801 TGGGCAGCCG GAGAACAACT ACAAGACCAC GCCTCCCGTG CTGGACTCCG

851 ACGGCTCCTT CTTCCTCTAT AGCAAGCTCA CCGTGGACAA GAGCAGGTGG

901 CAGCAGGGGA ACGTCTTCTC ATGCTCCGTG ATGCATGAGG CTCTGCACAA

951 CCACTACACG CAGAAGAGCC TCTCCCTGTC CCCGGGTAAA
```

All the producing cell lines were adapted and cultured in a protein free culture medium and the production were performed in rolling bottles or in fermentors. After the production, the monoclonal antibodies were purified by using protein-A affinity chromatography. The purified antibodies were then stored frozen at −20° C.

Rituxan (Rituximab) (Genentech, South San Francisco, Calif., USA) is a chimeric mouse/human anti-CD20 monoclonal antibody used in the treatment of patients with relapsed or refractory low-grade or follicular, CD20+, B-cell non-Hodgkin's lymphoma (NHL). Commercial Rituxan vials are stored at 2° C. to 8° C. in a sterile preservative-free solution at a concentration of 10 mg/ml.

AT10-FITC is a Fluorescein Isothiocyanate-labelled mouse monoclonal antibody directed to the binding site of FcgammaRIIA and FcgammaRIIB (AT10-FITC, Serotec, United Kingdom, Cat No MCA 1075F).

Immunofluorescence Binding Assay

First, recombinant human antibodies were complexed under polymeric forms for 30 min with affinity-purified goat F(ab)'$_2$ anti-human IgG (Jackson ImmunoResearch Laboratories Inc., West Grove, Pa., USA). 5×10$^5$ indicator cells were then incubated for 30 min with complexed antibodies in ice-cold phosphate-buffered saline containing 0.5% bovine serum albumin (PBS-BSA). Cells were then washed with PBS-BSA, and antibody binding was detected by incubation with FITC-labelled mouse F(ab)'$_2$ anti-human IgG (H+L) (Jackson ImmunoResearch) for 30 min on ice. After further washing, flow cytometry analysis was performed with a FACScalibur 4CA (Becton Dickinson, Mountain View, Calif., USA), using the Cell Quest Pro software.

Immunofluorescence Competition Assay

IIA1.6-huFcgammaRIIB cells were first incubated with various concentrations of monomeric LFB1, or monomeric LFB2, or monomeric LFB3, or monomeric Rituximab, and then with AT10-FITC. The binding of FITC-AT10 monoclonal antibody to human FcγRIIB in presence or absence of monomeric antibodies as competitors was then assessed by direct immunofluorescence. Flow cytometry analysis was performed with a FACScalibur 4CA (Becton Dickinson, Mountain View, Calif., USA), using the Cell Quest Pro software.

Facscalibur 4CA Technical Specifications

A 15 mW, 488 nm air cooled Argon-ion laser is used for acquisition of FITC fluorochrome. Estimated detection limit is 200 FITC equivalent molecules per particle. Logarithmic amplifiers for FL1 (FITC) provide four log decade range. Sorting speed is 300 cells/sec and the sorting purity is more than 95%.

Inhibition of Calcium Mobilization

IIA1.6-huFcgammaRIIB1 cells were incubated or not with LFB1 antibody for 30 min on ice. 10$^6$ cells were incubated with 5 mM Fluo-3 AM (Molecular Probes, Eugene, Oreg., USA) for 30 min at room temperature in RPMI 1640 containing 0.2% Pluronic F-127 (Sigma Chemicals Co., St. Louis, Mo., USA). The loaded cells were then washed three times with RPMI 1640 and adjusted to 10$^6$/ml. Cells were stimulated with rabbit F(ab')$_2$ anti-goat IgG (H+L) (RAG) (Jackson ImmunoResearch) alone or rabbit F(ab')$_2$ anti-goat IgG (H+L) (RAG) and goat F(ab')$_2$ anti-human IgG (H+L) (GAH) (Jackson ImmunoResearch) in RPMI 1640 containing 1 mM EGTA. After 150 sec of stimulation, 6 mM CaCl$_2$ were added. Intracellular calcium mobilization was detected by flow cytometry, performed with a FACScalibur 4CA, using the Cell Quest Pro software. Intracellular calcium concentrations means were then calculated with the FCS assistant 1.2.9 beta software (Becton Dickinson).

Inhibition of IL-2 Production

5×10$^5$ IIA1.6-huFcgammaRIIB1 cells were stimulated for 22h with F(ab')$_2$ rabbit anti-goat (Jackson ImmunoResearch) alone or with F(ab')2 rabbit anti-goat and LFB1, LFB2, or LFB3. The presence of mouse IL-2 was measured by ELISA assay, using 1 μg/ml rat anti-mouse IL-2 (Pharmingen) as capture antibody and 1 μg/ml biotinylated rat anti-mouse IL-2 (Pharmingen) as detection antibody.

The invention claimed is:

1. A method for the preparation of human, humanized or chimæric antibodies or polypeptides having different binding profiles, comprising an Fc region of human IgG, wherein said method comprises:
   a. providing candidate human, humanized or chimæric antibodies or polypeptides comprising the Fc region of human IgG produced naturally by or following transfection with a vector comprising the coding sequence for said antibody or polypeptide into animal cell lines comprising, EBV-transformed human B cell lines or from eukaryotic microorganisms,
   b. testing the binding of said antibodies or polypeptides on Fcgamma receptors FcgammaRIIIA, FcgammaRIIA and FcgammaRIIB, and
   c. selecting antibodies or polypeptides which:
      ii. bind to FcgammaRIIA and FcgammaRIIB but do not bind to FcgammaRIIIA or bind to FcgammaRIIIA with an ID50 superior or equal to 0.2 microM.

2. The method according to claim 1 wherein said antibodies or polypeptides selected in step:
   c. ii) are produced by cells from a non-lymphoid cell line.

3. The method according to claim 2, wherein
   iii. said non-lymphoid cell line is CHO (ATCC number CCL-61) or a cell line derived thereof.

4. The method according to claim 1, wherein said binding is performed using:
   i. indicator cells from a cell line that express different Fc receptors on their cell surface, or
   ii. recombinant Fc receptors comprising FcgammaR ectodomains, Fc receptors derived-peptides.

5. The method according to claim 1, wherein said antibodies or polypeptides selected for their ability to bind to FcgammaRIIA and FcgammaRIIB are further selected by a functional assays for their ability
   ii. to trigger FcgammaRIIB leading to the inhibition of calcium mobilization and to the inhibition of cytokine production such as IL-2 by cells expressing FcgammaRIIB such as B cells and monocytes.

6. The method of claim 5, wherein said functional assays consist of a calcium mobilization inhibition assay, and/or a cytokine secretion inhibition assay.

7. The method of claim 5, wherein said functional assay further comprises a specific FcgammaRIIIA ADCC assay.

8. A method of producing antibodies in a non-lymphoid cell line wherein said antibodies bind FcgammaRIIA and FcgammaIIB but do not bind to FcgammaRIIIA or bind to FcgammaRIIIA with an ID50 superior or equal to 0.2 microM.

9. The method of claim 8, wherein said antibodies are immunomodulatory antibodies.

10. The method of claim 8, wherein said antibodies induce ADCC and phagocytosis by monocytes and macrophages expressing FcgammaRIIA.

11. The method of claim 8, wherein said cells from a non-lymphoid cell line is CHO (ATCC number CCL-61).

12. The method of claim 6, wherein said functional assay further comprises a specific FcgammaRIIIA ADCC assay.

13. The method of claim 9, wherein said antibodies induce ADCC and phagocytosis by monocytes and macrophages expressing FcgammaRIIA.

* * * * *